US008581731B2

(12) United States Patent
Purks et al.

(10) Patent No.: US 8,581,731 B2
(45) Date of Patent: Nov. 12, 2013

(54) CIRCUITS, SYSTEMS, AND METHODS FOR MONITORING AND REPORTING FOOT IMPACT, FOOT PLACEMENT, SHOE LIFE, AND OTHER RUNNING/WALKING CHARACTERISTICS

(76) Inventors: Connor Kent Purks, Cary, NC (US);
Kory Patrick Purks, Cary, NC (US);
Bryce Benjamin Purks, Cary, NC (US);
Deborah Rhea Purks, Cary, NC (US);
David Kent Purks, Cary, NC (US)

( * ) Notice: Subject to any disclaimer, the term of this patent is extended or adjusted under 35 U.S.C. 154(b) by 353 days.

(21) Appl. No.: 12/932,056

(22) Filed: Feb. 16, 2011

(65) Prior Publication Data
US 2011/0140897 A1    Jun. 16, 2011

(51) Int. Cl.
*G08B 23/00* (2006.01)
(52) U.S. Cl.
USPC ............... 340/573.1; 340/573.7; 340/665
(58) Field of Classification Search
USPC ............ 340/573.1, 573.7, 665; 73/488, 490, 73/510, 865.4; 702/141, 150
See application file for complete search history.

(56) References Cited

U.S. PATENT DOCUMENTS

| | | | |
|---|---|---|---|
| 6,305,221 B1 * | 10/2001 | Hutchings | 73/510 |
| 7,355,519 B2 * | 4/2008 | Grold et al. | 340/573.7 |
| 7,827,000 B2 * | 11/2010 | Stirling et al. | 73/490 |
| 7,911,339 B2 * | 3/2011 | Vock et al. | 340/665 |
| 7,912,672 B2 * | 3/2011 | Feichtinger et al. | 702/150 |
| 2012/0041767 A1 * | 2/2012 | Hoffman et al. | 482/8 |

* cited by examiner

*Primary Examiner* — John A Tweel, Jr.
(74) *Attorney, Agent, or Firm* — David K. Purks

(57) ABSTRACT

Various embodiments of the present invention provide an electronic virtual running/walking coach that notifies a person as to how hard the person's feet have been impacting a surface, notifies the person as to whether the person's feet are impacting a surface at a proper relative distance from the body and/or at a proper side-to-side angle, and/or notifies the person as to how much cushioning life remains in a pair of shoes. When the notifications are provided to the person during the running/walking activity, the person can respond by taking immediate actions to adjust the foot placement relative to the body and/or adjust the level of foot impact to an acceptable level by varying the speed, step distance, and/or posture while running/walking and/or by selecting among different available surfaces on which to run/walk. A person may also more accurately determine when a particular pair of shoes should be replaced because they no longer provide a sufficient level of cushioning to compensate for the levels of foot impact that are occurring.

110 Claims, 12 Drawing Sheets

CIRCUITS, SYSTEMS, AND METHODS FOR MONITORING AND REPORTING FOOT IMPACT, FOOT PLACEMENT, SHOE LIFE, AND OTHER RUNNING/WALKING CHARACTERISTICS

FIELD OF THE INVENTION

This invention relates to monitoring athletic activity, and more particularly to apparatuses and methods for monitoring running activities.

BACKGROUND OF THE INVENTION

Over the course of a 5-K run, the average runner strikes the ground about 3,000 times, placing ground reaction force loads of 2 to 3 times the body weight on each leg and sending shock waves through the feet, legs, spine, and elsewhere. Because of this repetitive high-impact loading, many injuries are associated with running. The injuries can include "runner's knee" (pain in the knee), Shin splints, bone stress fractures, plantar fasciitis, and Achilles tendinitis. Repetitive stress in the same tissues/bones without enough time for recovery or running with improper form can lead to such injuries.

The advice generally given to runners to attempt to avoid such injuries is to warm up before exercising, use cross training with different speeds/distances/exercises as part of an exercise routine, run-on softer surfaces, use high-quality cushioned running shoes, and to replace running shoes often. Because the cushioning provided by running shoes wears out over time, avid runners are generally advised to replace running shoes every six months. In view of the high cost of quality running shoes, runners are presented with a dilemma of balancing the replacement cost of shoes with essentially a guesstimate as to when a particular pair of running shoes no longer provides sufficient cushioning and should be replaced before injury. Once a pair of shoes is replaced, it generally is never used again for running, although it may still provide sufficient cushioning for running on softer surfaces, such as on treadmills, gravel/dirt, or grass.

Consequently, there continues to be a tremendous need for further innovation that can assist runners with avoiding preventable injuries while enabling more cost effective use of running shoes.

SUMMARY OF THE INVENTION

Various embodiments of the present invention are directed to a foot impact monitoring system that functions as a electronic virtual running/walking coach that enables a person to more accurately and effectively regulate foot impact, improving foot placement, and/or determine remaining shoe life. The system can notify a person as to how hard the person's feet have been impacting a surface, notify the person as to whether the person's feet are impacting a surface at a proper relative distance from the body, and/or notify the person as to how much cushioning life remains in a pair of shoes. When the notifications are provided to the person during the running/walking activity, the person can respond by taking immediate actions to adjust the foot placement relative to the body and/or adjust the level of foot impact to an acceptable level by varying the speed, step distance, and/or posture while running/walking and/or by selecting among different available surfaces (e.g., concrete, treadmills, gravel/dirt, rubber coated, grass) on which to run/walk. A person may also more accurately determine when a particular pair of shoes should be replaced because they no longer provide a sufficient level of cushioning to compensate for the levels of foot impact that are occurring.

In some embodiments, a foot impact monitoring system includes an impact measurement circuit and an impact alert circuit. The impact measurement circuit is configured to measure impact from a foot repetitively striking a surface while a person is walking/running. The impact alert circuit is configured to respond to the measured impact by generating for the person an indication of how much impact is occurred from the foot striking the surface.

In some further embodiments, the impact alert circuit regulates a background sound component in response to a measured level of the impact, and combines the background sound component with a music component generated by a music player to generate a combined signal that is played to the person to audibly indicate to the person how much impact occurred from the foot striking the surface.

The impact alert circuit may be configured to increase loudness of the background sound component relative to the music component of the combined signal being played to the person in response to a presently measured level of the impact exceeding a baseline threshold level by an increased amount to audibly indicate to the person when the level of impact from the foot striking the surface has increased. Conversely, the impact alert circuit may decrease loudness of the background sound component relative the music component of the combined signal being played to the person in response to a presently measured level of the impact exceeding the baseline threshold level by a decreased amount to audibly indicate to the person when the level of impact from the foot striking the surface has decreased.

In some further embodiments, a sound generation device is configured to generate sound to the person. The impact alert circuit is further configured to generate a baseline threshold level in response to an average of measurements of the levels of impact, and to respond to a presently measured level of the impact exceeding the baseline threshold level by causing the sound generation device to generate a foot impact warning sound to the person.

The impact alert circuit may increase loudness and/or modify a defined tone characteristic of the foot impact warning sound generated by the sound generation device in response to a presently measured level of the impact exceeding the baseline threshold level by an increased amount to audibly indicate to the person when the level of impact from the foot striking the surface has increased. Conversely, the impact alert circuit may decrease loudness and/or oppositely modify the defined tone characteristic of the foot impact warning sound generated by the sound generation device in response to a presently measured level of the impact exceeding the baseline threshold level by a decreased amount to audibly indicate to the person when the level of impact from the foot striking the surface has decreased.

In some further embodiments, the foot impact monitoring system includes a display device that is configured to display indicia to the person. The impact alert circuit generate a record of the measured levels of impact and communicate the record of the measured levels of impact to the display device. The display device, via the impact alert circuit, graphs the measured levels of impact from the record relative to an elapsed time of the activity, a speed at which the person was walking/running, and/or a distance that the person walked/ran.

In some further embodiments, the impact alert circuit is configured to monitor the measured impact while the person is walking/running over the life of at least one of the person's shoes, and to generate an indication of when the shoe has become worn-out in response to how much the monitored impact measurements change over the life of the shoe. The impact alert circuit may respond to a calibration signal from a person by generating a baseline threshold level in response to an average of measurements of the levels of impact, and may generate an indication of when the shoe has become worn-out in response to how much the monitored acceleration measurements change relative to the baseline threshold level.

The impact alert circuit may be configured to respond to a calibration signal from a person by generating a baseline threshold level in response to an average of a rate of change of measurements of the levels of impact, and to generate an indication of when the shoe has become worn-out in response to a comparison of a rate of change of a present measurement of the level of impact to the baseline threshold level.

In some further embodiments, the impact alert circuit is further configured to determine from characteristics of the measured impact when the person is placing the foot excessively forward when striking the surface and resulting in excessive undesirable slowing forces exerted on the foot and retarding forward movement of the person. The impact alert circuit can generate an audible/visual warning to the person that an improper foot placement condition exists responsive to the determination that the person is placing the foot excessively forward when striking the surface. The impact alert circuit may determine that the person is placing the foot excessively forward when striking the surface in response to determining from the measured impact when acceleration greater than a defined threshold occurs in a direction opposite to a forward direction of movement of the person.

In some further embodiments, the impact alert circuit is further configured to determine from characteristics of the measured impact when the person is leaning the foot (ankle) inward (pronation) or outward (supination) when striking the surface and resulting in undesirable rotational forces exerted on the foot, ankle, and/or knee. The impact alert circuit can generate an audible/visual warning to the person that notifies the person of the foot leaning contact and may further provide an indication of the extent of the leaning (e.g., indicate supination (underpronation), neutral pronation, or overpronation).

Additional apparatuses and methods according to other embodiments of the invention will be or become apparent to one of skill in the art upon review of the following drawings and Detailed Description. It is intended that all such additional apparatus and methods be included within this description, be within the scope of the present invention, and be protected by the accompanying claims.

BRIEF DESCRIPTION OF THE DRAWINGS

The accompanying drawings, which are included to provide a further understanding of the invention and are incorporated in and constitute a part of this application, illustrate certain embodiments of the invention. In the drawings.

DETAILED DESCRIPTION

Figure 1:
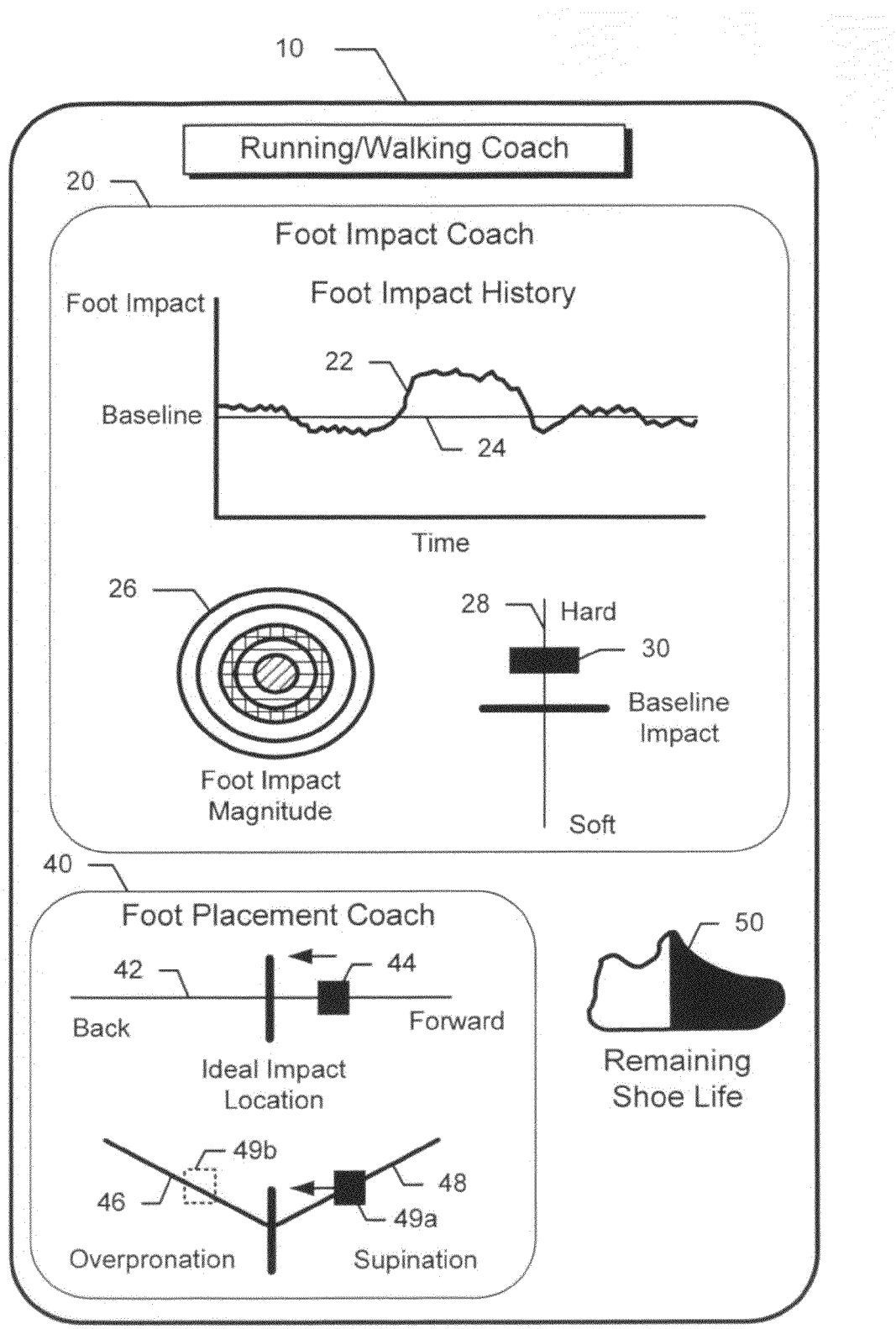
FIG. 1 illustrates example information that can be generated by a foot impact monitoring system for display on a display device to coach a runner/walker on reducing foot impact, improving foot placement, and/or advising as to remaining shoe life according to some embodiments of the present invention.

Embodiments of the present invention now will be described more fully hereinafter with reference to the accompanying drawings, in which embodiments of the invention are shown. This invention may, however, be embodied in many different forms and is not to be construed as limited to the embodiments set forth herein.

As explained above, many injuries are associated with running. While running, fatigue and other physiological changes (e.g., endorphins, aka "runner's high") can mask pain and other warning signs from bad running form, such as from excessively hard foot impact (e.g., stomping) and/or improperly impacting their feet too far ahead of the body. Bad running form can create high impact forces and/or vibration transmitted through the runner's shoes into the feet, legs, and body. These forces and vibration can cause "runner's knee" (pain in the knee), Shin splints, bone stress fractures, plantar fasciitis, Achilles tendinitis, back pain, etc.

Although runners are advised to frequently replace their running shoes to attempt to obtain sufficient cushioning, runners must balance the risk of injury with their guesstimate as to when a particular pair of running shoes no longer provides sufficient cushioning and needs replacement.

Various embodiments of the present invention are directed to an electronic foot impact monitoring system that functions as a running/walking coach that provides information to a runner/walker as to how hard their feet are impacting a surface, whether they are running/walking with proper foot placement relative to their body (e.g., foot impact too far ahead of body, rear foot impact, midfoot impact, forefoot impact), and/or determine and display how much useful cushioning life remains in shoes.

Various embodiments are described herein in the example context of providing real-time information to a person who is running/walking as to how the person's feet are impacting a surface so the person can adjust how hard the feet are impacting surface, can change what type of surface is run on (e.g., concrete, treadmills, gravel/dirt, rubber coated track, grass, etc.), can adjust where the feet are impacting the surface relative to their body (e.g. adjust how far ahead of their body), and/or determine when a particular pair of running shoes is nearing or has reached the end of its useful cushioning life. However, these embodiments are not limited to providing real-time information, and may additionally or alternatively be embodied in a foot impact monitoring system that provides information to the person after completion of a run/walk, such as by post-operations on a desktop computer, laptop computer, palmtop computer, tablet computer, smart phone, or other electronic device that may or may not be carried by the person while running/walking.

As used herein, the term "foot impact" refers to acceleration, rate of change or acceleration (e.g., jerk), force, and/or pressure that is applied to a foot responsive to striking a surface while running, walking, and/or jumping.

FIG. 1 illustrates an example informational display 10 that is generated on a display device to provide coaching to a runner/walker according to some embodiments of the present invention. Referring to FIG. 1, the informational display 10 can function as a foot impact coach and/or foot placement coach using information generated by a foot impact monitoring system as will be described below with regard to FIGS. 2-18. It is to be understood that the particular embodiments of FIG. 1 are provided as illustrative examples only, and that the invention is not limited thereto. Other information may be selected for display and may be displayed in other orientations and/or formats to provide the recited function of informing a person as to foot impact levels and/or foot placement.

Foot impact information display(s) 20 may include a foot impact history graph 22 that plots measured levels of foot impact while a person is running/jogging relative to a timeline. The impact history graph 22 may include a baseline threshold level 24 that is generated in response to an average of impact level measurements and/or which was set during a calibration process. For example, the foot impact monitoring system may determine the baseline threshold level 24 by averaging impact level measurements over a sufficient period of time (e.g., more than one minute) to develop a typical impact level for the particular person while running/walking at a typical speed, stride, etc. and for a particular pair of shoes. In some embodiments, the average impact level 24 is generated in response to the person triggering the foot impact monitoring system to enter a calibration mode during which a new/different pair of shoes is used to run at least a defined/suggested distance (e.g., several hundred feet or, in some embodiments, at least one mile) to develop a typical impact level for that person running/walking with the particular shoes. A person may additionally or alternatively trigger the foot impact monitoring system while running at a preferred foot impact level, speed, and/or stride and/or while running on a particular type of running surface (e.g., grass, treadmill, pavement, rubber surface track etc) to set the baseline 24 to which subsequent foot impact measurements can be compared against.

Accordingly, a person can view the foot impact history graph 22 to determine whether the person's feet are impacting the surface harder or softer relative to the baseline threshold level 24, and may thereby take actions to adjust the level of foot impact to a desired level, such as by adjusting the foot placement relative to the body, the speed, the step distance, and/or posture while running/walking, and/or by selecting among different available surfaces (e.g., concrete, treadmills, gravel/dirt, rubber coated, grass) on which to run/walk. When the foot impact monitoring system is carried by the person while running/walking, the person may dynamically view the impact history graph 22 and make adjustments so as to immediately provide an acceptable level of foot impact for the person.

The foot impact information display(s) 20 may alternatively or additionally include other types of graphical display of the present level of foot impact magnitude. For example, a present measurement of foot impact may be indicated by selectively shading concentric circles 26, with the innermost circle being shaded to indicate a relatively soft foot impact and successive outer circles being shaded to indicate that increases in foot impacts are occurring, or vice versa. Accordingly, a measured foot impact that is less than a first threshold can be indicated by shading the innermost circle, an impact that is greater than the first threshold and less than a larger second threshold communicated by shading the next radial outward circle, an impact that is greater than the second threshold and less than a less than a larger third threshold communicated by shading the next radial outward circle, and so on with threshold increases in foot impact causing further outward circles to be shaded, or vice versa (e.g., shading from the outmost circuit inward responsive to threshold measurement increases in foot impact).

The foot impact information display(s) 20 may alternatively or additionally include a linear graph 28 that illustrates a relative strength of a present foot impact. The graph 28 may illustrate a marker 30 that represents a present level of foot impact that has been measured while a person is running/walking, and which may be illustrated relative to a baseline impact level that may defined as described above for the baseline threshold level 24 or elsewhere for other determined baseline threshold level(s).

Accordingly, a person can view the concentric circles 26 and/or the linear graph 28 to determine whether the person's feet are impacting the surface harder or softer than desired, and may take immediate actions to adjust the level of foot impact to a desired level, such as by adjusting the foot placement relative to the body, the speed, the step distance, and/or posture while running/walking, and/or by selecting among different available surfaces on which to run/walk.

The foot impact information display(s) 20 may alternatively or additionally include a foot placement informational display 40 that can function as a foot placement coach while a person is running/walking or to provide useful feedback after completing the activity. The foot placement informational display 40 may for example include a linear graph 42 that illustrates a marker 44 that represents a present location of where the foot is striking a surface relative to an ideal impact location. The ideal impact location may be calibrated to correspond to a location relatively near the person's body that reduces backward impact forces against the feet and/or provides a desired foot strike location on the feet (e.g., rear foot, midfoot, forefoot strike location). When the foot impact monitoring system is carried by the person while running/walking, the person may dynamically view the foot placement informational display 40 and make adjustments to where the person's feet are striking the surface to avoid unnecessary impact forces/vibration on person's muscular, tendon, and skeletal structure of the feet, legs, and body.

The foot placement informational display 40 may alternatively or additionally provide information on whether the person is running/walking with overpronation or supination when the feet are impacting the surface, and may further indicate a relative amount of overpronation or supination that is occurring. For example, the information display 40 may include a graph 46,48 with a movable marker 49 that is moved along the graph 46,48 to indicate whether and to what extent the foot is impacting a surface with overpronation (distance of marker 49*a* along line 46 from ideal foot plant angle represented by vertical line), and to indicate whether and to what extent the foot is impacting a surface with supination (distance of marker 49*b* along line 48 from ideal foot plant angle represented by vertical line). The ideal foot plant angle may be calibrated for a particular person to compensate for the unique skeletal-muscular structure of a person that dictates what is a comfortable foot plant angle for that person. The calibration may be carried out in response to a user command while the person while running/walking with a comfortable foot placement, or may be carried out as an average or other numeric combination of sensed impact valued over a defined time period.

With a normal pronation (e.g., indicated by the vertical line) foot placement, the outside part of the heel makes initial contact with the ground. The foot "rolls" inward (e.g., about fifteen percent) and comes in complete contact with the ground. The rolling in of the foot optimally distributes the forces of impact, and is an important movement for proper impact absorption.

With an overpronation foot placement (e.g., marker 49*b* shown along line 46), the outside of the heel makes the initial ground contact and then the foot rolls inward more than an ideal amount (e.g., more than fifteen percent). Overpronation can cause the foot and ankle to have problems stabilizing the body, and provide poor impact absorption, and at the end of the gait cycle, the front of the foot pushes off the ground using mainly the big toe and second toe, which then must do all the work.

With a supination (underpronation) foot placement (e.g., marker 49*a* shown along line 48), the outside of the heel makes initial contact with the ground and then inward movement of the foot occurs at less than an ideal amount (e.g., less than fifteen percent), with resulting forces of impact being concentrated on a smaller area of the foot (the outside part) and not efficiently distributed. In the push-off phase, most of the work is done by the smaller toes on the outside of the foot.

The foot impact information display(s) 20 may alternatively or additionally include indicia that indicate when a particular pair of running shoes no longer provides sufficient cushioning and should be replaced before onset of occurrence of one or more running related injuries. For example, a shoe outline (or other graphical object) 50 can be filled-in (or emptied) to graphically indicate how much cushioning life remains in a particular pair of shoes. A filled-in shoe outline 50 (or emptied outline) may thereby indicate that the shoes should be replaced because they no longer provide a sufficient level of cushioning.

The information display 10 of FIG. 1 is provided as a non-limited example to illustrate various embodiments and does not limit the scope of the invention. It is to be understood that history graphs may be provided for various other analysis of the foot impact display 20 (e.g., history graphs may be provided instead of or in addition to the graphs 26 and 28), and may be graphed relative to time, distance run/walked, speed, stride step distance, etc to allow a person to develop an understanding of how their foot impact measurements can vary with the various running/walking parameters. For example, the person may be able to determine from the displayed information that their foot impact becomes excessive at certain running speeds, such as due to a longer stride step distance, and can therefore adapt their running speed or allowed duration at that speed when running/walking on some types of surfaces based on that information. The person may alternatively or additionally determine from the displayed information that their foot impact is excessive during a warm-up phase of running, such as due to insufficient stretching, or near the end of a run, such as due to fatigue, and may thereby adapt their warm-up phase or end-run phase (e.g., select a softer running surface, run at a speed/stride distance that provides lower impact) to reduce the foot impact.

It is to be further understood that time history graphs may be provided for various other analysis of the foot placement displays 40 (e.g., history graphs may be provided instead of or in addition to the graphs 42 and 46,48), and may be graphed relative to time, distance run/walked, speed, stride step distance, etc to allow a person to develop an understanding of how their foot placement measurements can vary with the various running/walking parameters. For example, the person may be able to determine from the displayed information that their foot overpronation becomes excessive at certain running speeds, such as due to a longer stride step distance, and can therefore adapt their running speed or allowed duration at that speed when running/walking on some types of surfaces based on that information. The person may alternatively or additionally determine from the displayed information that overpronation/supination is excessive during a warm-up phase of running, such as due to insufficient stretching, or near the end of a run, such as due to fatigue, and may thereby adapt their warm-up phase or end-run phase (e.g., select a softer running surface, run at a speed/stride distance) to reduce the excessive overpronation/supination.

Figure 2:
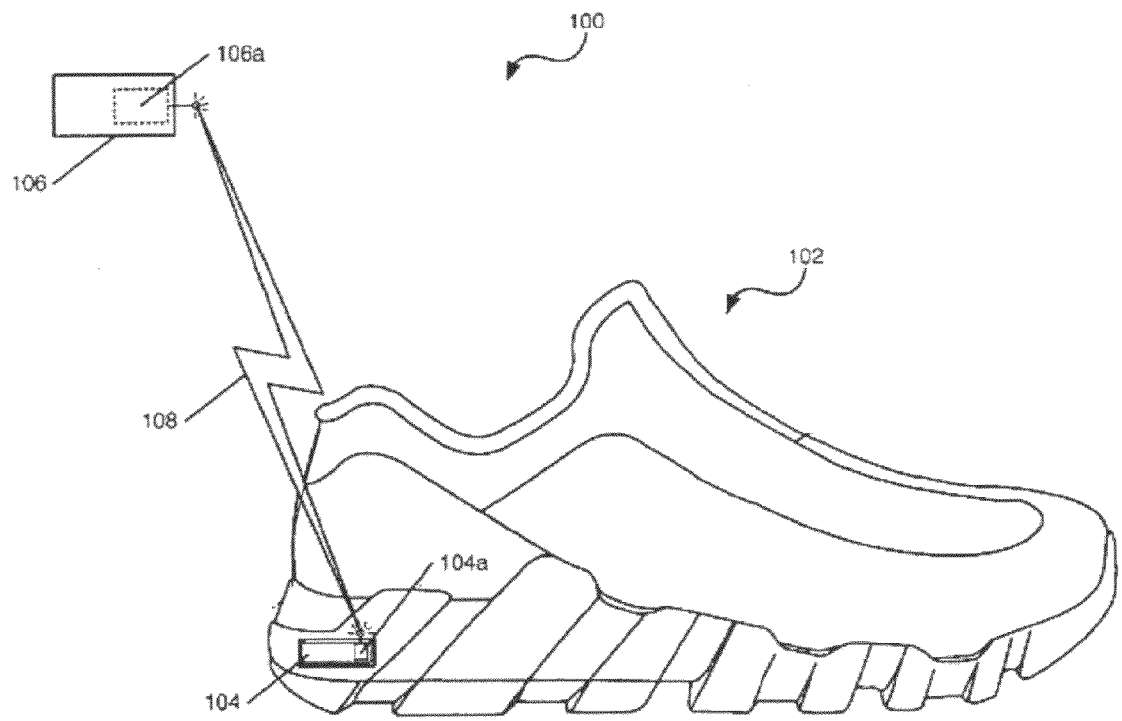
FIG. 2 illustrates an example impact measurement circuit that is within a shoe and wirelessly communicates to an impact alert circuit according to some embodiments of the present invention.

FIG. 2 illustrates an example impact measurement circuit 104 that is connected to a shoe 102 and wirelessly communicates impact measurements to an impact alert circuit 106 according to some embodiments of the present invention. The impact measurement circuit 104 is configured to measure impact from the shoe 102 striking a surface while a person is walking/running and/or to determine an angle of the leg/foot when the foot impacts the surface.

The impact measurement circuit 106 may include an accelerometer that is configured to measure impact from the foot striking the surface while the person is walking/running. Alternatively or additionally, the impact measurement circuit 104 may include a force transducer that is configured to measure force from the foot striking the surface while the person is walking/running. The force transducer may, for example, be configured to output a signal that indicates a measurement of the force, strain, and/or pressure in the material of the shoe sole (e.g., rubber sole) as the material compresses/expands responsive to the shoe impacting a surface. The impact measurement circuit 106 may be configured to generate a signal that indicates a peak magnitude of the measured impact.

The impact measurement circuit 104 may additionally or alternatively include a tilt sensor that measures angle/tilt of the shoe/foot/leg when the shoe 102 impacts a surface, and may communicate the measured angle/tilt to the impact alert circuit 106 for use in determining foot positioning relative to the body at impact. The tilt sensor may include, but is not limited to, a multi-axis accelerometer, a multi-axis force transducer, mechanical movement device (e.g., rolling ball with position sensors), or other inclinometer or sensor. The impact measurement circuit may include one multi-axis sensor or may include spaced apart single-axis or multi-axis impact sensors (e.g., spaced apart in the direction of forward movement of the shoe) that can measure the back-to-front or front-to-back progression of the impact as the foot impacts a surface and rolls forward/backward.

The impact measurement circuit 104 may reside in one or more discrete packages that are, for example, connected to the shoe 102, and/or it may include a plurality of sensor elements that are spaced apart on the shoe to, for example, measure characteristics of the impact as the shoe rolls forward after impacting a surface and/or to measure characteristics of the impact as the shoe rolls inward/outward (e.g., due to pronation/supination) after impacting the surface. Accordingly, impact sensors may be spaced apart at locations in a heal portion and midfoot/forefoot location of the shoe, and/or impact sensors may be spaced apart at locations in a right and left portion of the shoe.

The impact measurement circuit 104 includes a transmitter circuit 104a that transmits the measured impacts to the impact alert circuit 106, which includes a receiver circuit 106a to receive the measurements. The measurements may be transmitted through a wireless air interface using one or more wireless protocols, such as, without limitation, Bluetooth, near field communication (NFC), WIFI (e.g., IEEE 802.11). The impact measurement circuit may be configured to be mounted/connected/embedded within a heel (rear) region of the person's shoe to increase sensitivity of the impact measurement from the foot striking a surface while the person is walking/running. Although the impact measurement circuit 104 is illustrated in FIG. 2 as being within a heel region of the shoe, the invention is not limited thereto because the impact measurement circuit 104 may reside in a mid-foot region or forefoot region of the shoe 102 or may be connected elsewhere on a person's body. For example, the impact measurement circuit 104 may be configured to be connected a person's ankle or leg (e.g., via a strap) or elsewhere that will provide sufficient sensitivity to changes in foot impact levels (e.g., impact magnitude), such as on a person's head or central body to sense accelerations/vibration transferred from the feet through a person's spine.

The impact alert circuit 106 is configured to notify the person as to how hard/soft the person's foot is impacting a surface, how much cushioning life remains in shoes, whether/how much the foot is impacting the surface relative to a preferable location relative to the body, and/or provide other information regarding foot placement on the surface, such as whether/how much the foot is impacting the surface at a rear-foot location, mid-foot location, forefoot location and/or whether/how much the foot is impacting the surface tilted to the right of left at impact.

Figure 3:
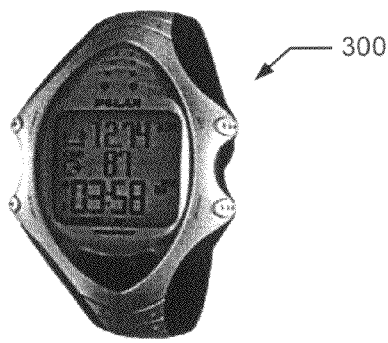
FIG. 3 illustrates a wrist watch that is configured to inform a person of characteristics of their foot impacting a surface while running/walking according to some embodiments of the present invention.
Figure 4:
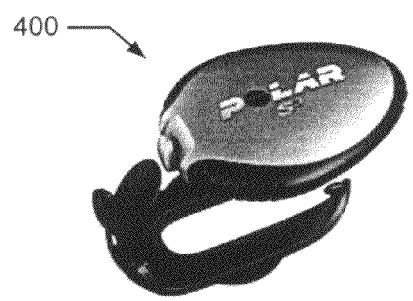
FIG. 4 illustrates an example impact measurement circuit that can be connected to a shoe and configured measure foot impact levels as a person is running/walking according to some embodiments of the present invention.
Figure 5:
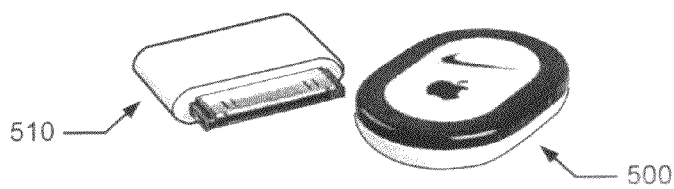
FIG. 5 illustrates another example impact measurement circuit configured according to some embodiments of the present invention.

FIGS. 3-5 illustrate various embodiments of impact measurement circuits and impact alert circuits that can be configured to operate as described herein. The invention is not limited to these example embodiments.

FIG. 3 illustrates a wrist watch 300 that includes an impact alert circuit that informs a person of characteristics of the foot impacting a surface while running/walking according to some embodiments of the present invention. The wrist watch 300 includes an informational display device that is configured to provide coaching to a runner/walker, such as by generating one or more of the information indicia of FIG. 1 or other indicia according to some embodiments of the present invention. The wrist watch 300 may include a sound generation device that is configured to generate sound to the person that audibly indicates a level of impact (e.g., an average level of impact or peak magnitude of impact) that is occurring when one/both of the person's feet are striking a surface.

FIG. 4 illustrates an example impact measurement circuit 400 that can be connected to a shoe (e.g., to the laces) to measure foot impact levels as a person is running/walking, and to transmit the measurements to a separate impact alert circuit (e.g., the watch 300 of FIG. 3) and/or to locally stored the measurements in a log file that can be later downloaded to an impact alert circuit (e.g., a personal computer, etc.). The log file may include individual impact measurements and/or may store one or more accumulated impact metric that are generated by algorithmically combining (e.g., averaging, weighted averaging, arithmetic mean, geometric mean, harmonic mean, median, trending, etc.) individual impact measurements to generate an accumulated impact metric.

FIG. 5 illustrates another example impact measurement circuit 500 that can be connected to a shoe to measure a foot impact levels of person is running/walking, and to transmit the measurements to a receiver device 510 that is communicatively connected to a separate impact alert circuit. The impact measurement circuit 500 may be placed within the shoe, such as within or below a running pad in a heel region of the shoe (e.g., as shown in FIG. 2).

Figure 6:
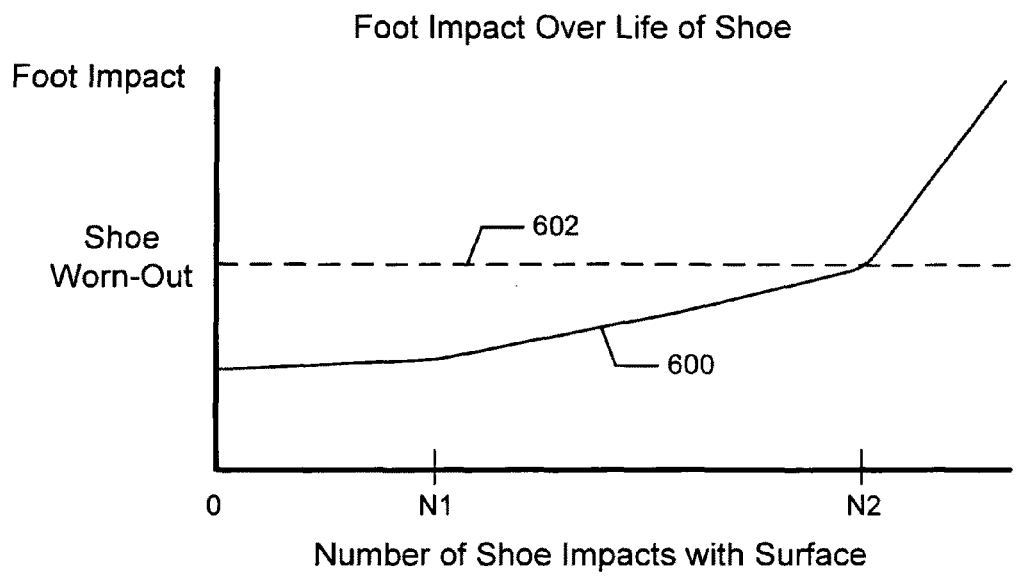
FIG. 6 is a graph that illustrates how the average impacts exerted on a foot while running/walking can substantially increase over the lifetime of a running shoe.

FIG. 6 is a graph 600 that illustrates how the average impact exerted on a foot while running/walking can substantially increase over the lifetime of a running shoe, represented by the number of surface impacts on the shoe. Referring to FIG. 6, a new shoe generally provides the greatest relative cushioning as the insole (which may be a removable pad on which the foot rests) and the thick midsole (e.g., layer of rubber or other supportive materials) function to cushion the feet by reducing the peak magnitude of the impacts between the shoe and surfaces as a person runs/walks. However, as the number of impacts increases (e.g., more than N1) the insole wears-out by failing to provide much impact cushioning relative to when the shoe was new (e.g., low relative use). As the number of impacts increases (e.g., between N1 and N2), the thick midsole continues to cushion the feet by reducing the peak impact magnitudes, however the level of cushioning gradually decreases with a corresponding increase in the impact magnitude experienced by the feet (e.g., illustrated by the first rate of increasing impact magnitude). In contrast, when the thick midsole wears-out (e.g., as the impacts approach N2), the shoe no longer provides sufficient impact cushioning for the feet and the peak impact magnitudes rapidly increase with continued use of the shoe, illustrated by the much greater second rate of increase of impact magnitude after N2 impacts with the average impacts exceeding a "worn-out" threshold 602. Continued use of the shoe for running or other higher impact activities may result in one or more of the above-described injuries due to much higher impact forces and/or vibrations traveling through the feet, legs, and body of the person. Accordingly, the trend of the impact levels over time or the rate of change in the trend can be used by the impact monitoring system to determine how much cushioning life remains in a pair of shoes.

In accordance with some embodiments, the foot impact monitoring system is configured to respond to a calibration signal from a person (e.g., by a person entering a command to calibrate the system for a new or different pair of shoes) by generating a baseline threshold level in response to an average of measurements of the levels of impact. Thus, the system may generate a baseline threshold level of the impact measurements while the shoes are providing good cushioning (e.g., between 0 and N1 in FIG. 6). The system can further generate an indication of how much shoe life remains (e.g., the shoe life indication 50 in FIG. 1) in response to the measured levels of impact over a defined number of impacts and the baseline threshold level. The system may alternatively or additionally display a warning on a display device and/or generate an audible warning when the shoe is determined to have become worn-out based on how much the monitored acceleration measurements have changed relative to the baseline threshold level. Accordingly, the system can inform a person how much cushioning life remains in a shoe and/or notify the person when the shoe no longer provides an acceptable level of cushioning by comparing the presently measured impacts to the baseline threshold level.

Alternatively or additionally, the system may generate an indication of how much shoe life remains and/or notify a person that a shoe has become worn-out in response to determining that the rate of change in the measured impacts has increased more than a threshold amount. For example, when the system determines that the rate of change in the peak magnitude of the impacts has increased from an average rate between N1 and N2 to a greater rate of change after N2, the system can determine therefrom that the shoe no longer provides sufficient impact cushioning for the feet and the peak impact magnitudes rapidly increase with continued use of the shoe.

Figure 7:
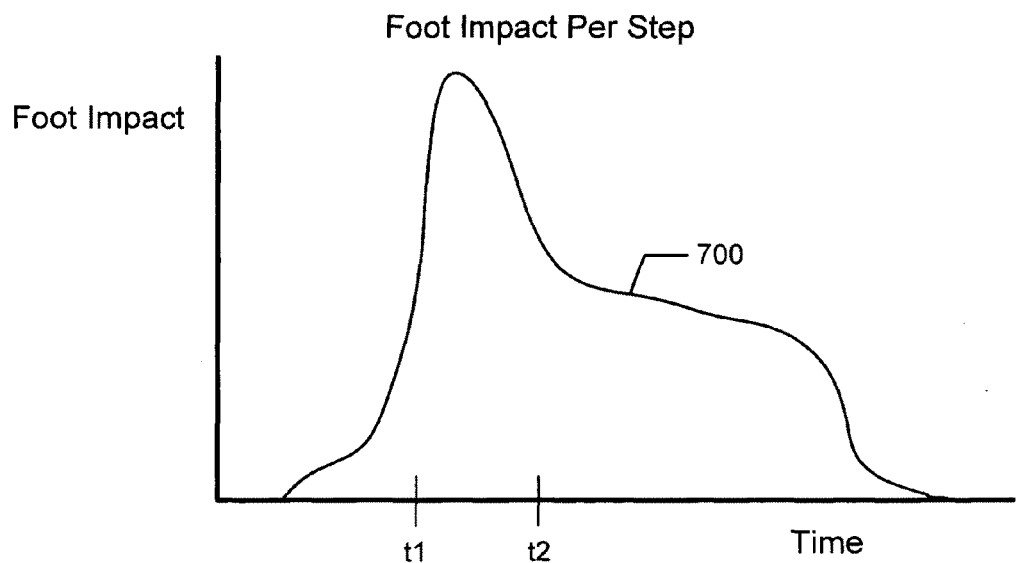
FIG. 7 is a graph that illustrates a single impact experienced by a foot relative to time from the foot striking a surface while a person is running.

FIG. 7 is a graph 700 that illustrates an example curve/trend in impact measurements during a single impact experienced by a foot relative to time from the foot striking a surface while a person is running. The impact force and acceleration rapidly increases from when the shoe initially impacts a surface (e.g., with a heal strike) to a peak magnitude, between time T1 and T2, as the sole of the shoe rapidly compresses to absorb some of the impact. The foot impact then more gradually decreases from the peak magnitude as the foot rolls forward (e.g., from a heal strike to mid-foot and then forefoot) compressing other regions of the sole of the shoe, and then the foot leaves the ground to be positioned for the next impact while the person is running/walking. In some embodiments, the impact alert circuit is configured to generate an indication to the person of a foot impact level in response to a peak magnitude of the measured impact, which may be particularly important information for the person to know in order to be able to adapt how the person is running/walking to avoid injury (e.g., by reducing the peak impact magnitude by stepping softer, impact the feet more under the body instead of in-front of the body, etc.).

The impact alert circuit may compare a magnitude, average, or other measurement associated with the peak pulse segment (e.g., between T1 and T2) to a magnitude, average, or other measurement of another segment of the impact (e.g., outside of the peak pulse (e.g., from T2 to the end of the measured impact) or inclusive of the peak pulse) to generate information that is used to regulate notifications of the impact level experienced when the foot impacts a surface. Because the measured impact level will vary with weight of the runner, comparison of peak pulse segment to the entire impact waveform or another segment outside of the peak pulse segment may enable the impact alert circuit to at least partially remove bias that is introduced into the measurements due to the person's weight. The impact alert circuit may, for example, be configured to respond to an increase in the difference from the comparison by indicating to the person that the foot impact has increased, and conversely may respond to a decrease in the difference from the comparison by indicating to the person that the foot impact has decreased. The impact alert circuit may alternatively or additionally be configured to respond to the difference from the comparison exceeding one or more defined thresholds by generating an excessive foot impact warning sound and/or displayed indicia (graphical or textual indication on a display device) indicating to the person that the foot impact has become excessive.

FIG. 7 may alternatively or additionally represent the level of impact or stress experience by a foot that impacting a surface and then rolling inward/outward due to excessive overpronation/supination. In some embodiments, the impact measurement circuit is configured to measure the sideways rolling impact for use by the impact alert circuit. The impact measurement circuit may include one multi-axis sensor or may include spaced apart single-axis or multi-axis impact sensors that can measure the sideways progression of the impact as the foot impacts a surface and rolls sideways. The impact alert circuit is configured to generate an indication for the person of whether and/or how much overpronation/supination is occurring based on the peak magnitude of the measured impact, based on the sideways acceleration, or other characteristics that reflect the rolling movement of the shoe due to overpronation/supination.

When used for monitoring sideways rolling movement (overpronation/supination), the impact alert circuit may compare a magnitude, average, or other measurement associated with the peak pulse segment (e.g., between T1 and T2) to a magnitude, average, or other measurement of another segment of the impact (e.g., outside of the peak pulse (e.g., from T2 to the end of the measured impact) or inclusive of the peak pulse) to generate information that is used to regulate notifications of the level of overpronation/supination experienced when the foot impacts a surface. Because the curve/trend in the measured impact levels will vary with weight of the runner, comparison of peak pulse segment to the entire impact waveform or another segment outside of the peak pulse segment may enable the impact alert circuit to at least partially remove bias that is introduced into the measurements due to the person's weight. The impact alert circuit may, for example, be configured to respond to an increase in the difference from the comparison by indicating to the person that the foot overpronation/supination has increased, and conversely may respond to a decrease in the difference from the comparison by indicating to the person that the foot overpronation/supination has decreased. The impact alert circuit may alternatively or additionally be configured to respond to the difference from the comparison exceeding one or more defined thresholds by generating an excessive foot overpronation/supination warning sound and/or displayed indicia (graphical or textual indication on a display device) indicating to the person that the foot overpronation/supination has become excessive.

Figure 8:
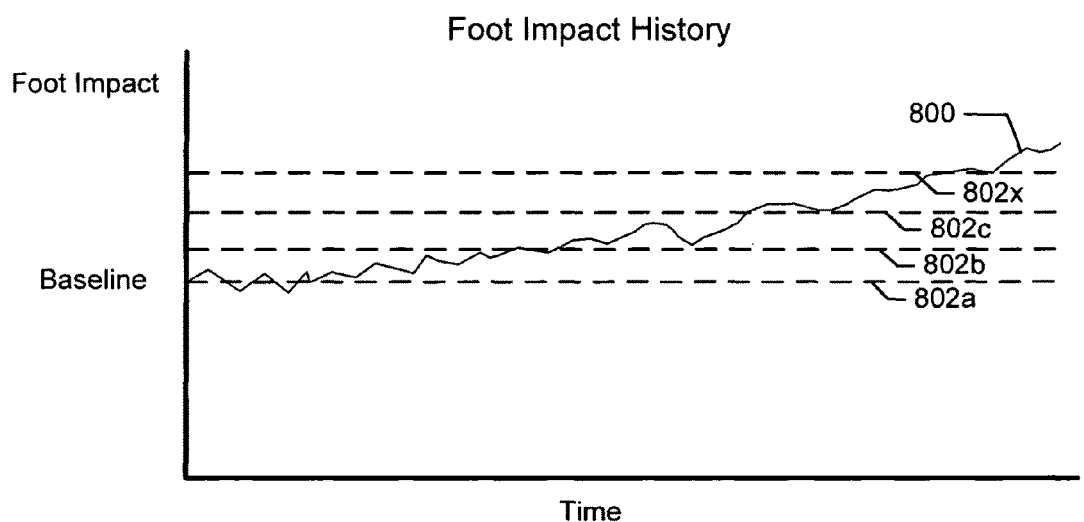
FIG. 8 is a graph that illustrates how the level of impact experienced by a foot while running can vary with hardness of the running surface, the speed of the runner, and fatigue of the runner.

FIG. 8 is a graph that illustrates how the level of impact 800 experienced by a foot while running can vary with hardness of the running surface, the speed of the runner, and fatigue of the runner. In some embodiments, the foot impact monitoring system is configured to generate a baseline threshold level in response to an average of measurements of the levels of impact. The average may be made over an initial calibration timeframe (e.g., baseline level 802*a*), and/or may be a running average over a defined interval (e.g., more than one minute or, in some embodiments, more than ten minutes to filter out minor variations that occur while running/walking) to repetitively generate baseline levels (e.g., baseline levels 802*b-x*). The system may then generate an audible notification and/or display a visual notification that informs the person whether they are experiencing a higher or lower foot impact than the baseline threshold level. In some embodiments, the impact alert circuit is configured to graph the measured levels of impact relative to an elapsed time of the activity (e.g., to generate a foot impact graph, such as the example graph 800 of FIG. 8), and may further display the impact levels relative to a speed at which the person was walking/running and/or a distance that the person walked/ran. The person may thereby analyze whether excessive foot impact levels are occurring at certain running/walking speeds, occurring as a result of fatigue, occurring on certain sloped segments of a route taken by the person, and/or occurring on certain types of surfaces traversed by the person, and may respond by taking corrective actions.

Figure 9A:
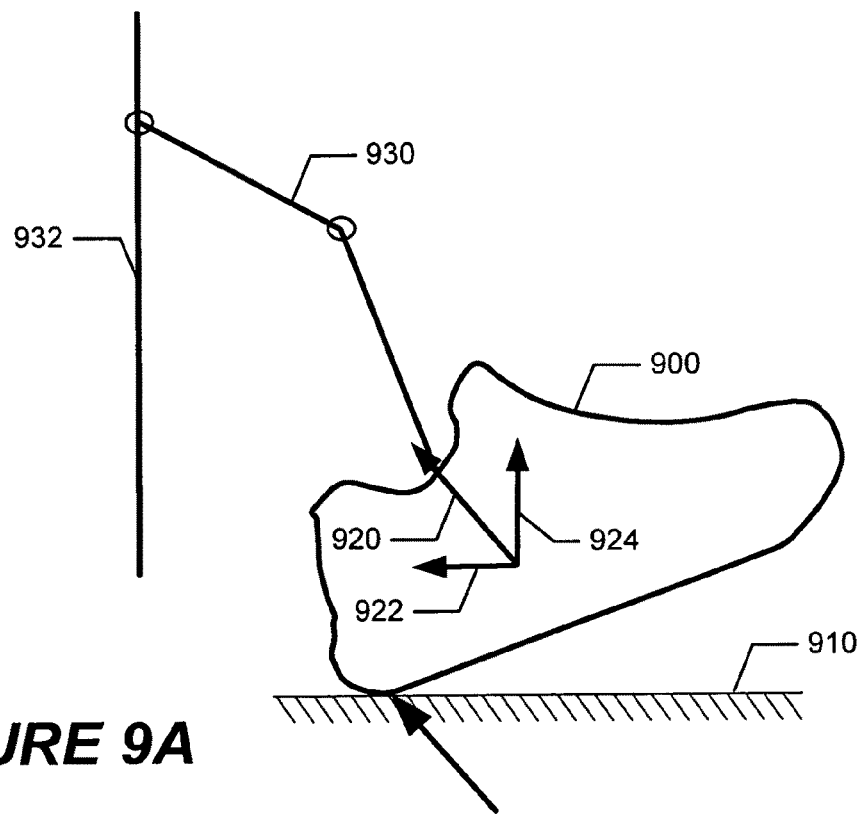
FIG. 9A illustrates using a side view of a shoe how improper foot placement too far ahead of the person's body while running/walking results can result in an unnecessary impact component force into the foot and leg and an unnecessary impact component force that retards forward movement of the runner/walker.

FIG. 9A illustrates what happens when a person runs/walks by improperly impacting a foot 900 with a surface 910 too far ahead of the person's body 932. Because the foot 900 is impacting too far ahead of the body 932, a resultant force 920 is created is angled backward from the direction of movement and has an undesirable horizontal force component 922 opposite to the direction of movement along with a vertical force component 924. The opposite horizontal force component 922 retards forward movement of the person and, coupled through the moment arm between the point of contact and the ankle/knee and hip, creates rotational moment forces that undesirably stress bones, tendons, and muscles in the foot, ankle, shin, knee, and hip.

In accordance with some embodiments, the impact alert circuit is further configured to determine from characteristics of the measured impact when the person is placing a foot 900 excessively forward when striking the surface 910 and resulting in excessive undesirable slowing forces exerted on the foot 900 and retarding forward movement of the person. The impact alert circuit can generate an audible/visual warning to the person that an improper foot placement condition exists responsive to the determination that the person is placing the foot excessively forward when striking the surface 910. The impact alert circuit may determine from acceleration, pressure, and/or force measurements by an impact measurements circuit when the angle of the impact force indicates that the foot 900 is striking the surface 910 too far ahead of the body 932, and can provide audible/visually guidance to the person as actions are taken changing the relative impact distance of the foot 900 from the body to reduce the horizontal force component 922 to an acceptable level. In some embodiments, the impact alert circuit is configured to use a measured horizontal and/or vertical component of the impact to determine where the feet are impact the surface relative to the body. In some other embodiments, the impact measurement circuit includes a tilt sensor that measures an angle of the leg/foot when the foot impacts the surface, and communicates the measured angle to the impact alert circuit for use in determining where the feet are impact the surface relative to the body or another reference location. The impact measurement circuit may compare an impact measurement in a rear portion of the shoe to an impact measurement in forward portion of the shoe to generate an indication of whether and to what extent the shoe is impacting heel first, midfoot first, or toe first, and can generate an audible sound and/or display a graphical/textual indication to the person of a result of the analysis.

For example, with reference to FIG. 1, the impact alert circuit may generate the foot placement coach display 40 and regulate distance between the displayed marker 44, which represents a present location of where the foot 900 is striking the surface 910 relative to an ideal impact location (e.g., location 932). When the backward horizontal force component 922 and/or angle of impact decreases, the impact alert circuit may display the marker 44 closer to the ideal impact location (vertical line in display 40). Conversely, the impact alert circuit may display the marker 44 further ahead of the ideal impact location responsive to measurement of an increasing backward horizontal force component 922 and/or greater angle at impact. The ideal impact location may be calibrated to correspond to a location near the person's body that reduces backward horizontal force component 922 against the foot 900 and/or provides a desired foot strike location on the foot 900 (e.g., rear foot, midfoot, forefoot strike location). When the foot impact monitoring system is carried by the person while running/walking, the person may dynamically view the foot placement informational display 40 and make adjustments with where the foot 900 is striking the surface 910 to avoid unnecessary impact forces/vibration on person's muscular, tendon, and skeletal structure of the feet, legs, and body.

In some other embodiments, the impact measurement circuit can include a tilt sensor that measures an angle of the shoe 900 relative to the direction of movement (i.e., frontward/backward angle) when the shoe 900 impacts the surface 910, and communicates the measured angle to the impact alert circuit for use in determining whether and/or how much the foot is impacting the surface at a rear-foot location, mid-foot location, forefoot location. For example, when the impact measurement circuit determines that the shoe 900 is impacting the surface 910 angled significantly upward (e.g., relative to one or more threshold angle values), the impact alert circuit may respond thereto by generating an audible notification (e.g., tone) and/or visual notification (e.g., display text/graphical object) to the person that the person is running/walking with an excessive rear-foot heel strike angle. Alternatively, when the impact measurement circuit determines that the shoe 900 is impacting the surface 910 angled relatively flat (e.g., relative to one or more threshold angle values), the impact alert circuit may respond thereto by generating an audible notification (e.g., tone) and/or visual notification (e.g., display text/graphical object) to the person that the person is running/walking with an a mid-foot (e.g., flat foot) strike angle. Similarly, when the impact measurement circuit determines that the shoe 900 is impacting the surface 910 angled relatively downward (e.g., relative to one or more threshold angle values), the impact alert circuit may respond thereto by generating an audible notification (e.g., tone) and/or visual notification (e.g., display text/graphical object) to the person that the person is running/walking with a forefoot (e.g., toe) strike angle.

Running with a heel foot strike, if excessive, may aggravate the calf muscles and Achilles tendon and contribute to over-striding, slower running, and poorer form. Midfoot strike may provide better impact absorption due to a bent-leg, and provide less stress on the calf muscles and Achilles tendon. Toe strike may provide less stress on the knees and ankles and provide faster running form, however it may also contribute to shin splints, Achilles tendinitis and muscle pulls from maintaining the calf muscle contracted. The present notification may enable a person to dynamically adjust the foot placement with quantitative feedback from the impact alert circuit.

The impact measurement circuit may combine impact measurements with impact measurements to determine whether the impact angle indicates that this particular person is running/walking with an undesirable (e.g., injury prone or energy wasteful form). For example, when the measurements indicate that the shoe 900 is impacting the surface 910 with a downward angle and the impact has a threshold rearward component, the impact measurement circuit may notify the person that the shoe 900 is being dragged forward, which not only wastes energy while running, but which also may create unnecessary stress on the lower leg and be prone to leading to a fall if the shoe 900 catches a rock/crack/etc on the surface 910.

Figure 9B:
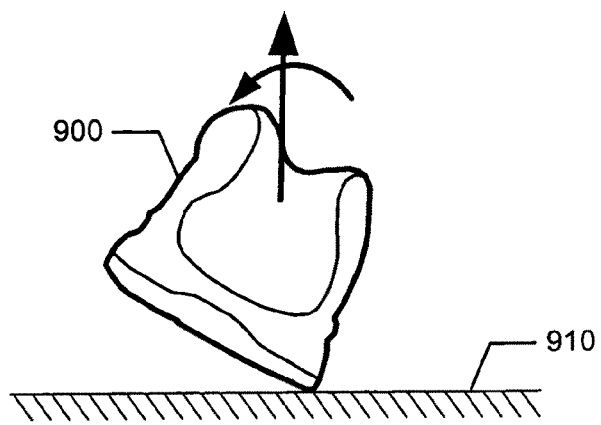
FIG. 9B illustrates using a rear view of a shoe how improper foot placement at an angle causing overpronation or supination while running/walking results can result in undesirable rotational forces on the foot and leg.

FIG. 9B illustrates how improper foot placement at an angle causing overpronation or, alternatively, supination while running/walking results can result in undesirable rotational forces on the foot and leg. In some other embodiments, the impact measurement circuit can include a tilt sensor that measures an angle and/or rolling movement of the shoe 900 side-to-side (i.e., angled toward right/left) when the shoe 900 impacts the surface 910, and communicates the measured angle and/or movement to the impact alert circuit for use in determining whether and/or how much the foot tilted toward the right/left when impacting the surface 910 (e.g., whether and/or how much the foot is impacting with overpronation, normal pronation, or supination). The impact measurement circuit may generate an audible notification (e.g., tone) and/or visual notification (e.g., display text/graphical object) to the person that indicates whether the shoe 900 is impacting with an undesirable angle, and may provide an indication of whether the shoe is moving through an overpronation, normal pronation, or underpronation cycle upon impact, and may provide a further indication of how far the shoe 900 is over-pronating or underpronating (e.g., using the overpronation/supination graph 46-49 of FIG. 1 or another graphical or textual indication of the measured condition). This notification may enable a person to actively adjust the foot placement, such as in real-time, (e.g., by running with feet closer together or further apart, increasing or decreasing the step stride, and/or regulating the allowed angle of the ankle-foot by conscious control of ankle muscles) to improve the motion of the feet and avoid stress and related injuries that can result when improperly angled feet are forced to roll inward/outward with each surface impact.

Figure 10:
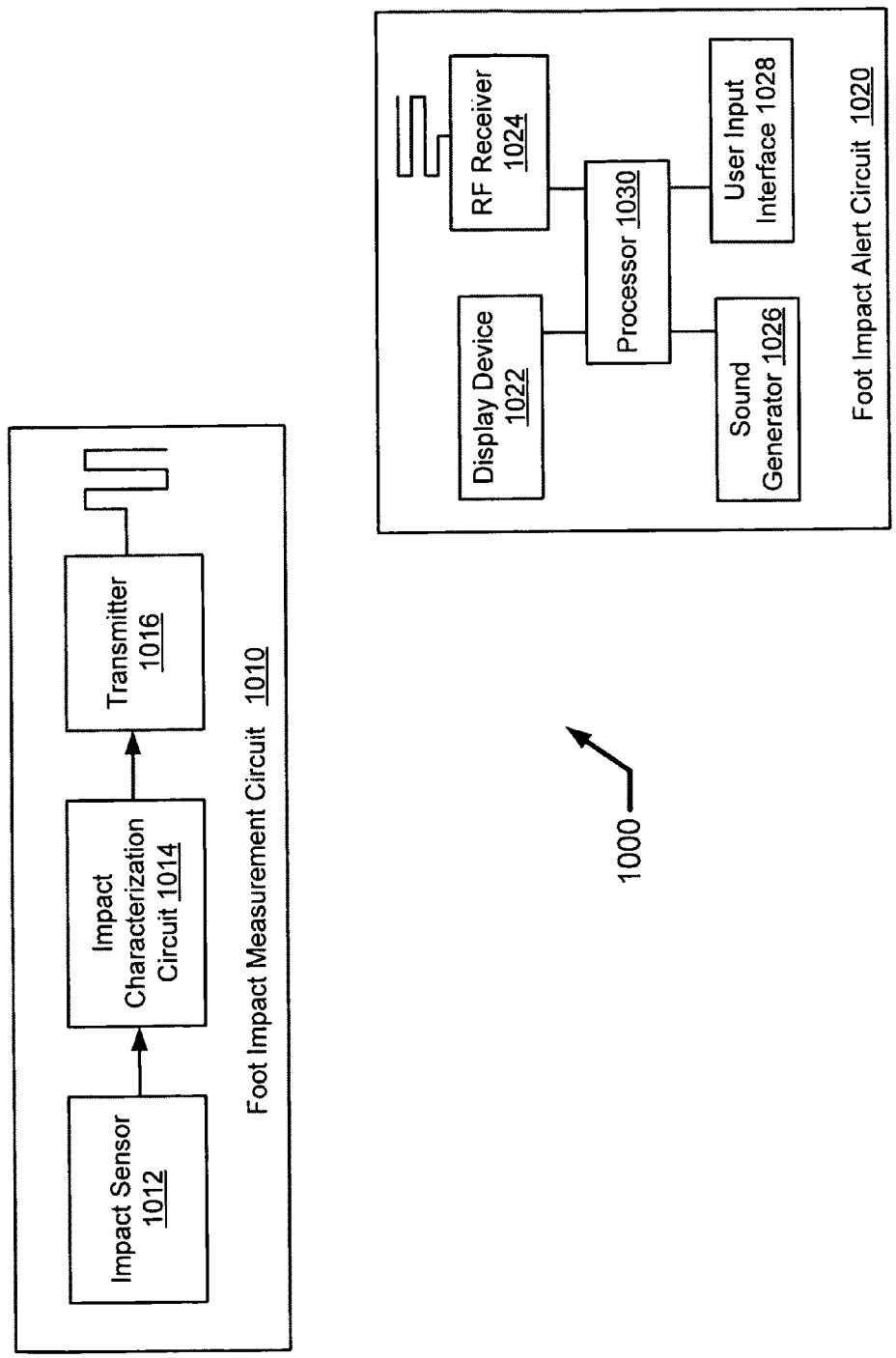
FIG. 10 is a block diagram of a foot impact monitoring system according to some embodiments of the present invention.

FIG. 10 is a block diagram of a foot impact monitoring system 1000 according to some embodiments of the present invention. The foot impact monitoring system 1000 includes a foot impact measurement circuit 1010 and a foot impact alert circuit 1020. The measurement circuit 1010 includes an impact sensor 1012, an impact characterization circuit 1014, and a transmitter 1016. The impact sensor 1012 may include an accelerometer that is configured to measure impact from the foot striking the surface while the person is walking/running. Alternatively or additionally, the impact sensor 1012 may include a force transducer that is configured to measure force from the foot striking the surface while the person is walking/running. The force transducer may, for example, be configured to output a signal that indicates a measurement of the force, strain, and/or pressure in the material of the shoe sole (e.g., rubber sole) as the material flexes responsive to the shoe impacting a surface. The impact measurement circuit 1010 may be configured to generate a signal that indicates a peak magnitude of the measured impact.

The impact measurement circuit 1010 may include a tilt sensor that measures angle/tilt of the foot/leg when the foot impacts a surface, and may communicate the measured angle/tilt to the impact alert circuit 1020 for use in determining foot positioning relative to the body at impact. The tilt sensor may include, but is not limited to, a multi-axis accelerometer, a multi-axis force transducer, mechanical movement device (e.g., rolling ball with position sensors), or other inclinometer or sensor.

The impact measurement circuit 1010 may include a piezo-electric transducer, potentiometric (e.g., spring-mass system), reluctive (e.g., inductive bridge), strain gauge, and/or capacitive device that outputs a signal that indicates a level of the measured impact.

The impact characterization circuit 1014, which is optional, may filter the signal from the impact sensor 1012 to generate a signal appropriate for transmission, and may covert the signal from an analog signal to a digital representation that can be transmitted as a digital signal through the transmitter 1016 and a wireless interface to the foot impact alert circuit 1020. The impact characterization circuit 1014 may average or otherwise combine the output signal from impact sensor 1012 over to a defined time interval to output a signal for transmission via the transmitter 1016. The transmitter 1016 may use one or more wireless protocols, such as, without limitation, Bluetooth, near field communication (NFC), WIFI (e.g., 802.11), to transmit the measured impact to the alert circuit 1020.

The foot impact alert circuit 1020 may include a display device 1022, a RF receiver 1024, a sound generation device 1026, and a user input interface 1028 there are controlled by a processor 1030. The RF receiver 1024 is configured to receive the measured impact information from the foot impact measurement circuit 1010.

The display device 1022 is configured to display foot impact information, foot placement information, remaining shoe cushioning life information, and/or other information that can be useful to a person while the person is running/walking and/or for review after completing the activity.

The sound generation device 1026 is configured to generate an audible signal that communicates foot impact information, foot placement information, remaining shoe cushioning life information, and/or other information that can be useful to a person while the person is running/walking and/or for review after completing the activity.

The user input interface 1028 is configured to receive commands from the user, such as a command to generate the baseline threshold level for a new or different pair of shoes, against which other measurements are compared to determine whether excessive foot impact occurring, improper foot placement is occurring, and/or to determine remaining shoe cushioning life.

The processor 1030 may include one or more data processing circuits, such as a general purpose and/or special purpose processor (e.g., microprocessor and/or digital signal processor). The processor 1030 is configured to execute computer program instructions from memory circuitry/devices, described herein as a computer readable medium, to perform some or all of the operations and methods that are described herein for one or more of the embodiments disclosed herein. Accordingly, the processor 1030 can be configured by execution of the computer program instructions to carry out at least some of the functionality described herein to respond to the impact measurements by generating an indication of how much impact occurred from a foot striking a surface, and other functionality described herein.

Although the foot impact measurement circuit 1010 and the foot impact alert circuit 1020 have been shown as being separate devices that communicate through a wireless interface, the invention is not limited thereto. In some embodiments, the foot impact measurement circuit 1010 and the foot impact alert circuit 1020 may be combined within a single physical device package, or some of the functionality described herein may be combined into a single physical device package. For example, some or all of the analysis of the impact measurements by the impact sensor 1012 described herein may be carried out within the foot impact measurement circuit 1010, such within the impact characterization circuit 1014, and the output of the analysis may then be communicated to the foot impact alert circuit 1020 for display on the display device 1022 and/or to control the sound generator 1026 to output notifications to the person. Alternatively, the impact measurement analysis, the display functionality, and/or the sound generation functionality described herein for analyzing or notifying a person may be carried out within the same physical package, and which may be attached to the shoe, ankle, leg, head, or elsewhere on the person where the desired functionality can be performed.

Figure 11:
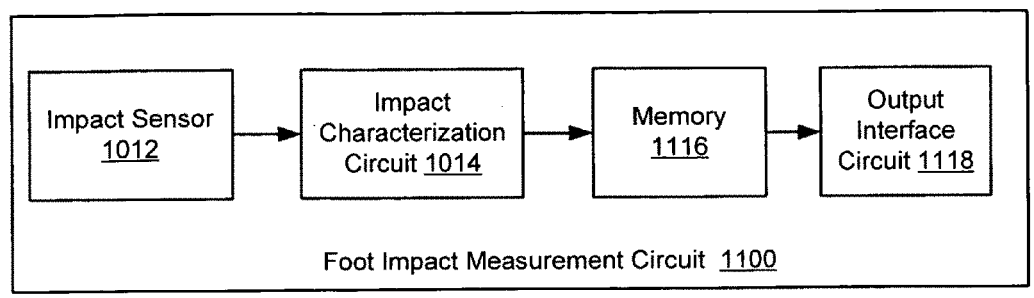
FIG. 11 is a block diagram of a foot impact measurement circuit that logs foot impact measurements according to some embodiments of the present invention.

FIG. 11 is a block diagram of another embodiment of a foot impact measurement circuit 1100 that logs foot impact measurements according to some embodiments of the present invention. The measurement circuit 1100 may include the impact sensor 1012 and the characterization circuit 1014 of FIG. 10. However, in contrast to the measurement circuit 1010 of FIG. 10, the measurement circuit 1100 of FIG. 11 is configured to locally store the impact measurements in a memory 1116 as a measurement log, instead of transmitting them in real-time to a foot impact alert circuit. Accordingly, after the person has completed an activity, the measurement log can be downloaded from the memory 1116 through an output interface circuit 1118 (e.g., a USB interface or other serial/parallel wired/wireless interface) to a foot impact alert circuit.

Figure 12:
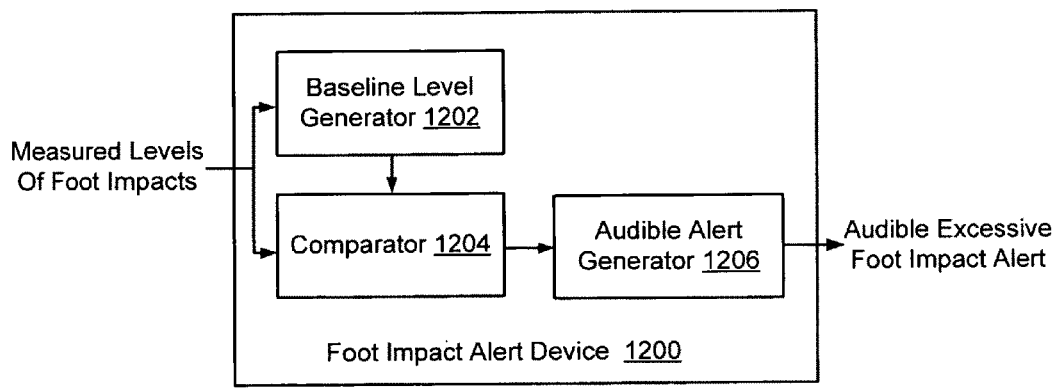
FIG. 12 is a block diagram of a foot impact alert circuit that generates audible foot impact notifications according to some embodiments of the present invention.

FIG. 12 is a block diagram of another embodiment of a foot impact alert circuit 1100 that generates audible foot impact notifications according to some embodiments of the present invention. The alert circuit 1200 can include a baseline level generator 1202, comparator 1204, and an audible alert generator 1206. The baseline level generator 1202 is configured to generate a baseline threshold level in response to an average of measurements of the levels of impact, which are received from a foot impact measurement circuit. The baseline level generator 1202 may respond to a calibration signal from a person (e.g., by a person entering a command to calibrate the system for a new or different pair of shoes) by generating a baseline threshold level in response to an average of measurements of the levels of impact. Alternatively or additionally, the baseline level generator 1202 may generate the baseline threshold level as a running average over a defined interval.

The comparator 1204 may compare measured levels of foot impact to the baseline threshold level and cause the audible alert generator 1206 to generate an audible foot impact warning sound that informs the person whether he/she is experiencing a higher or lower foot impact than the baseline threshold level (e.g., when the measured levels of impact exceed the baseline threshold level).

Accordingly, using the foot impact alert circuit 1200 of FIG. 12, the person can be audibly warned when the person's feet are impacting the surface at levels that exceed a baseline threshold level. The person may cause calibration of the baseline threshold level while the person is running with a pair of shoes having a desired level of cushioning and/or while the person is running with a level of foot impact that the person finds to be in a acceptable level and/or an upper range of an acceptable level, above which the person wants the circuit 1200 to provide an audible warning so that the person can take action to reduce the impact levels.

Figure 13:
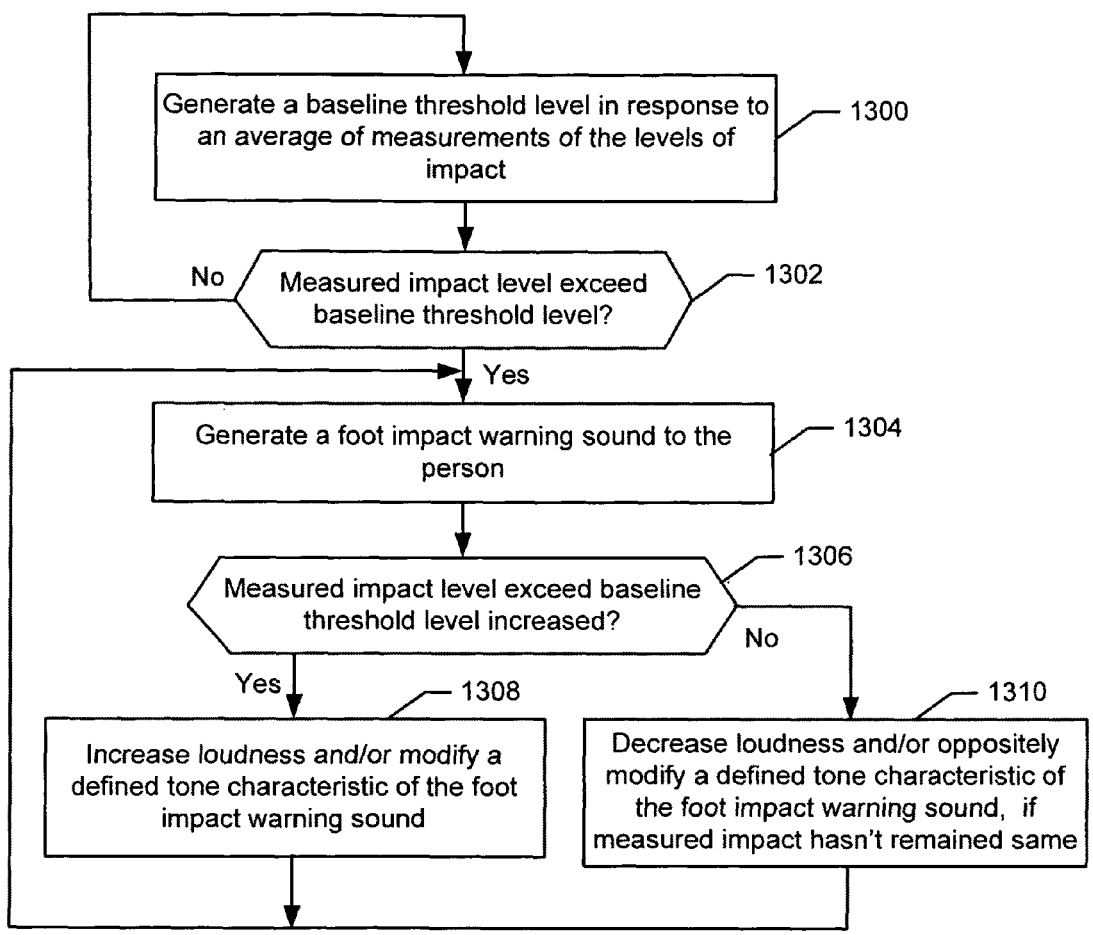
FIG. 13 is a flowchart of operations and methods for generating a foot impact warning sound to a person and regulates loudness and/or tone of the sound responsive to measured levels of foot impact while walking/running.

FIG. 13 is a flowchart of operations and methods for generating a foot impact warning sound to a person and regulates loudness and/or tone of the sound responsive to measured levels of foot impact while walking/running. Referring to FIG. 13, a foot impact alert circuit (e.g., alert circuit 1200) generates (block 1300) a baseline threshold level in response to an average of measurements of the levels of impact. A decision (block 1302) is made as to whether the measured impact level exceeds the baseline threshold level and, if so, a foot impact warning sound is generated (block 1304) to the person. The operations may include a further decision (block 1306) is made as to whether the measured impact level exceeds the baseline threshold level by an increasing or decreasing amount.

When the measured level of the impact exceeds the baseline threshold level by an increased amount, the impact alert circuit 1200 responds (block 1308) by increasing loudness and/or modifying a defined tone characteristic (e.g., increase/decrease frequency, pitch, etc.) of the foot impact warning sound generated by the sound generation device to audibly indicate to the person when the level of impact from the foot striking the surface has increased. In contrast, when the measured level of the impact exceeds the baseline threshold level by a decreased amount, the impact alert circuit 1200 responds (block 1310) by decreasing loudness and/or oppositely modifying the defined tone characteristic (e.g., decrease/increase frequency, pitch, etc.) of the foot impact warning sound generated by the sound generation device to audibly indicate to the person when the level of impact from the foot striking the surface has decreased. When the measure level of the impact has not changed relative to the baseline threshold level, the defined tone may be maintained as having the previous iteration characteristics.

Figure 14:
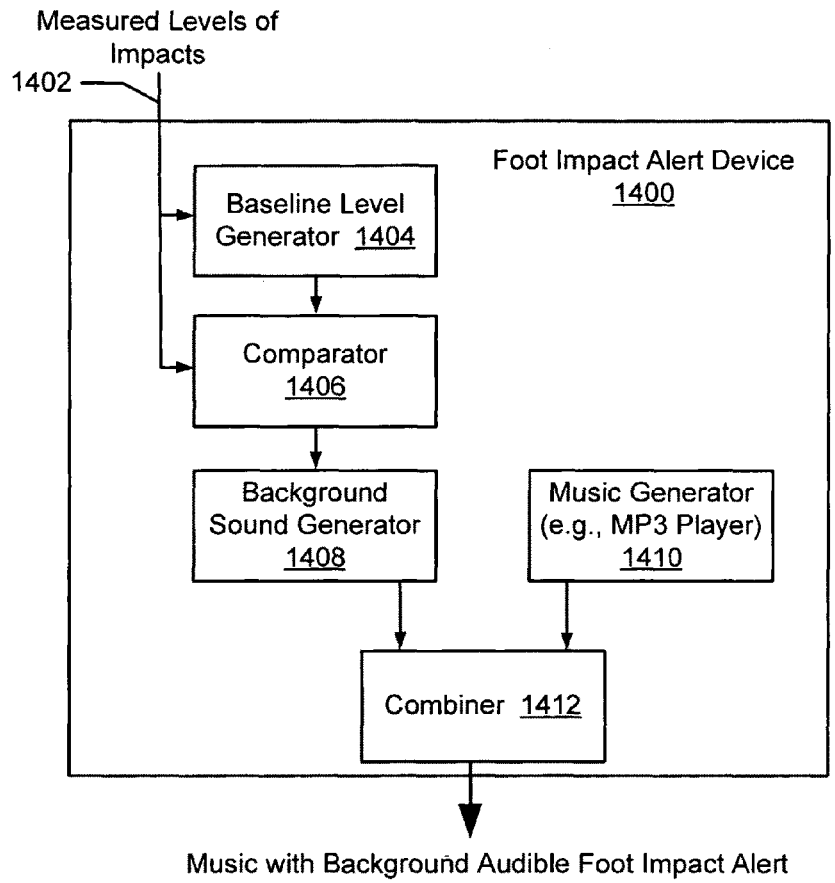
FIG. 14 is a block diagram of a foot impact alert circuit that is configured to combine background sound and music played through a music player to provide audible notification of measured foot impact levels while running/walking according to some embodiments of the present invention.
Figure 15:
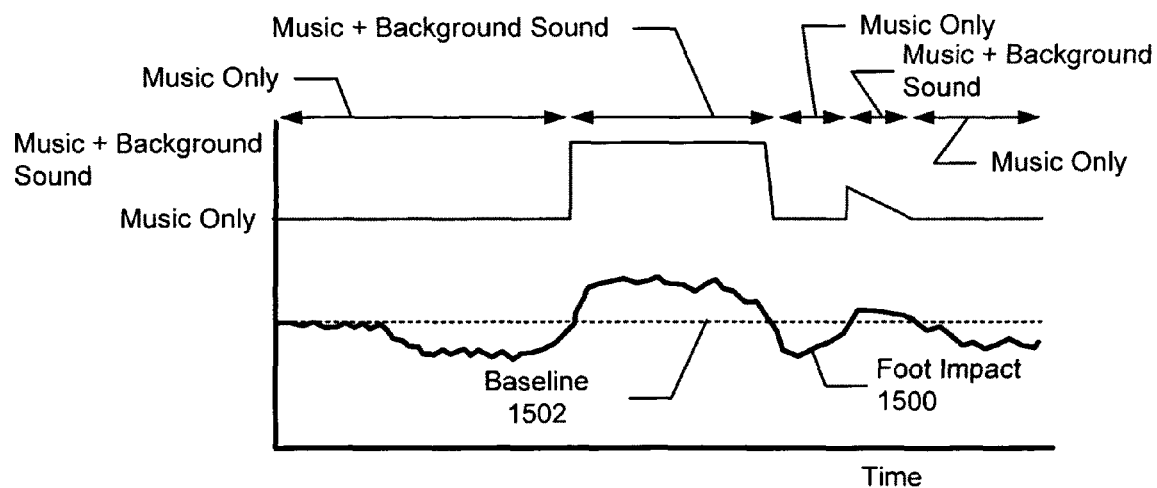
FIG. 15 illustrates graphs that show when only-music or a combination of music and background is played responsive to the measured foot impact levels according to some embodiments of the present invention.
Figure 16:
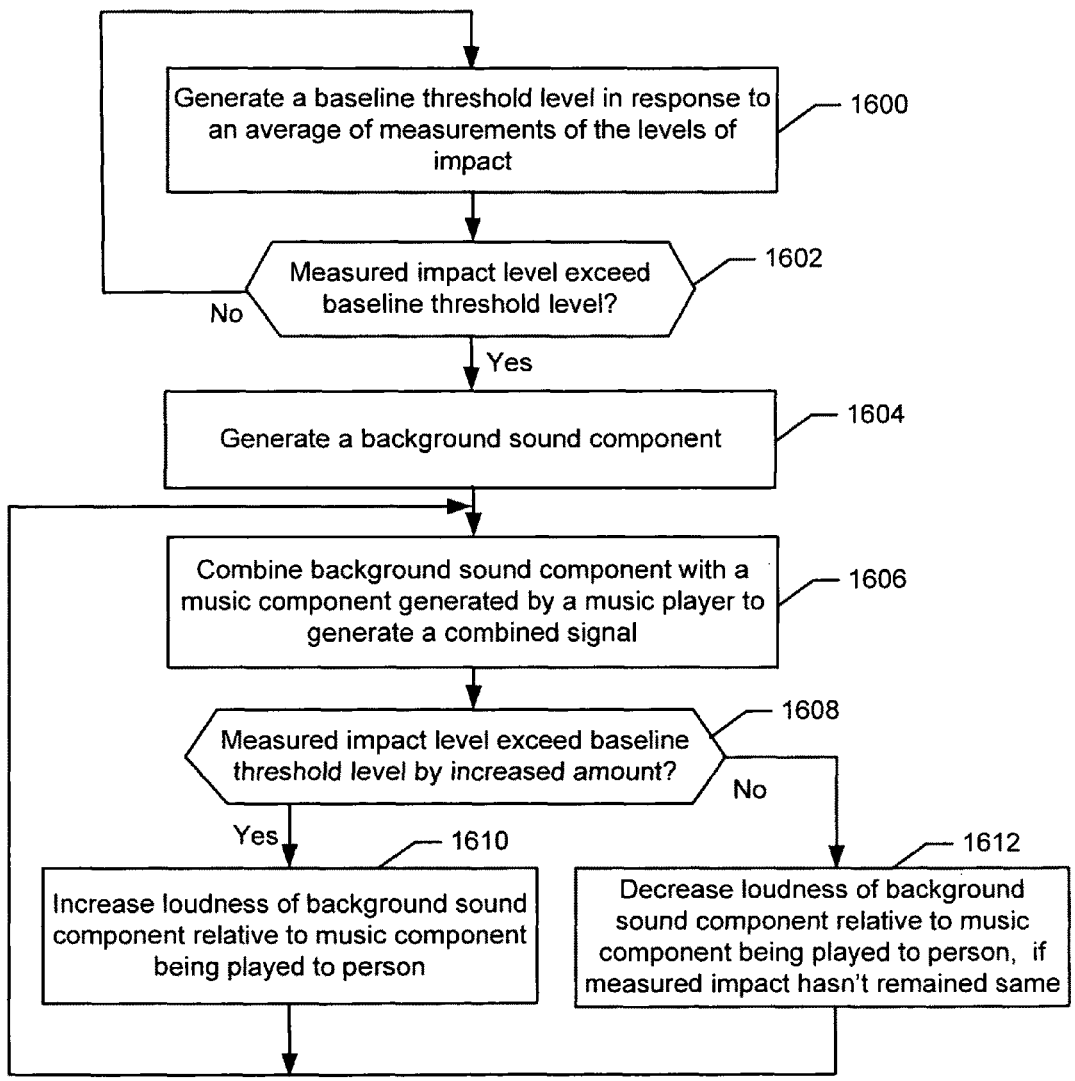
FIG. 16 is a flowchart of operations and methods that combine background sound and music played through a music player to provide audible notification of measured foot impact levels while running/walking according to some embodiments of the present invention.

FIG. 14 is a block diagram of a foot impact alert circuit 1400 that combines background sound and music played through a music player to provide audible notification of measured foot impact levels while a person is running/walking, according to some embodiments of the present invention. FIG. 15 illustrates graphs that show when only-music or a combination of music and background is played through a speaker to a person responsive to the measured foot impact levels, according to some embodiments of the present invention. FIG. 16 is a flowchart of operations and methods that combine background sound and music played through a music player to provide audible notification of measured foot impact levels while a person is running/walking, according to some embodiments of the present invention.

Referring to FIGS. 14-16, the foot impact alert circuit 1400 receives measurements 1402 of levels of foot impact from a foot impact measurement circuit. The foot impact alert circuit 1400 includes a baseline level generator 1404, the comparator 1406, the background sound generator 1408, a music generator 1410, and a combiner 1412.

The baseline level generator 1404 generates (block 1600 of FIG. 16) a baseline threshold level in response to an average of measurements 1402 of levels of foot impact. The generator 1404 may respond to a calibration signal from a person (e.g., by a person entering a command to calibrate the system for a new or different pair of shoes) by generating a baseline threshold level in response to an average of measurements of the levels of impact. Alternatively or additionally, the baseline level generator 1404 may generate the baseline threshold level as a running average over a defined interval (e.g., over at least one minute to filter out minor variations that occur while running/walking).

The comparator 1406 may compare (block 1602 of FIG. 16) measurements 1402 of levels of foot impact to the baseline threshold level. The comparator 1406 may respond to a presently measured impact level exceeding the baseline threshold level by causing the background sound generator 1408 to generate (block 1604 of FIG. 16) a background sound component. The combiner 1412 combines (block 1606 of FIG. 16) the background sound component with a musical component, that is output by the music generator 1410, to generate a combined signal that is output to a person, via a speaker that may be within the alert circuit 1400 and/or connected thereto by the wired connection and/or wireless connection, to audibly indicate to the person how much impact occurred from the foot striking the surface.

The music generator 1410 may include, but is not limited to, a digital music player (e.g., a MP3/WMA/AIFF/or other digital format music player), a video player (e.g., MPEG, DVD, Blue-Ray, or other video player), a broadcast (terrestrial/satellite/internet/cable) radio receiver, and/or a broadcast (terrestrial/satellite/internet/cable) television/movie/video receiver.

Although some of the functional blocks of FIG. 14 have been illustrated as being separate blocks, they are not limited thereto because their functionality may be combined in fewer or greater numbers of functional elements. For example, some or all of the functional blocks of FIG. 14 may be combined into one device, such as the music generator 1410. In one embodiment, the combiner 1412 may be connected (e.g., as a two-input-one-output Y-connector) to an output of the music generator 1410 (e.g., a headset output jack output) to add the background sound component to the output of the music generator 1410, and the output of the combiner 1412 may be fed to headphones or another sound generation device.

The operations may include a further decision (block 1608) as to whether the measured impact level exceeds the baseline threshold level by an increasing or decreasing amount.

When the measured level of the impact exceeds the baseline threshold level by an increased amount, the impact alert circuit 1400 responds (block 1610) by increasing loudness of the background sound component relative to the music component of the combined signal being played to the person in response to a presently measured level of the impact exceeding the baseline threshold level by an increased amount to audibly indicate to the person when the level of impact from the foot striking the surface has increased. In contrast, when the measured level of the impact exceeds the baseline threshold level by a decreased amount, the impact alert circuit 1400 responds (block 1612) by decreasing loudness of the background sound component relative the music component of the combined signal being played to the person in response to a presently measured level of the impact exceeding the baseline threshold level by a decreased amount to audibly indicate to the person when the level of impact from the foot striking the surface has decreased. When the measure level of the impact has not changed relative to the baseline threshold level, the background sound component may be maintained at the previous iteration characteristics.

The background sound that is generated by the background sound generator 1408 may be any sound that can be identified by a user as in indication of the measured foot impacts. For example, the background sound may be a white noise (e.g., flat power spectral density) that can be added to the sound component to generate the combined signal that is played to the person. Alternatively or additionally, the background sound may be a repeating tone (e.g., a drum beat).

While a person is running, the background sound can controlled to be louder (e.g., a louder static noise sound combined with the music component) to indicate when the feet are impacting the surface harder, and can controlled to be quieter (e.g., a level static noise sound combined with the music component) to indicate when the feet are impacting the surface softer. Alternatively or additionally, the background sound can controlled to have an increased/decreased frequency and/or pitch (e.g., a faster tone beat and/or sharper tone combined with the music component) to indicate when the feet are impacting the surface harder, and can controlled to have a decreased/increased frequency and/or pitch (e.g., a slower tone beat and/or duller tone combined with the music component) to indicate when the feet are impacting the surface softer.

Referring to the example graphs of FIG. 15, illustrates graphs that show when only-music or a combination of music and background is played responsive to the measured foot impact levels according to some embodiments of the present invention. A graph of the measured foot impact levels 1500 are plotted relative to a baseline threshold level 1502. While the measured foot impact levels 1500 are less than the baseline 1502, the foot impact alert generator 1400 may respond by outputting from the combiner 1412 only the music component (e.g., no background sound component). In contrast, while the measured foot impact levels 1500 are greater than the baseline 1502, the foot impact alert generator 1400 may respond by outputting from the combiner 1412 a combined signal that includes the background sound component and the music component. The alert generator 1400 may further regulate the relative magnitude (e.g., loudness) of the background sound component relative to the music component in the output combined signal in responsive how much the measured foot impact levels 1500 exceed the baseline 1502.

Figure 17:
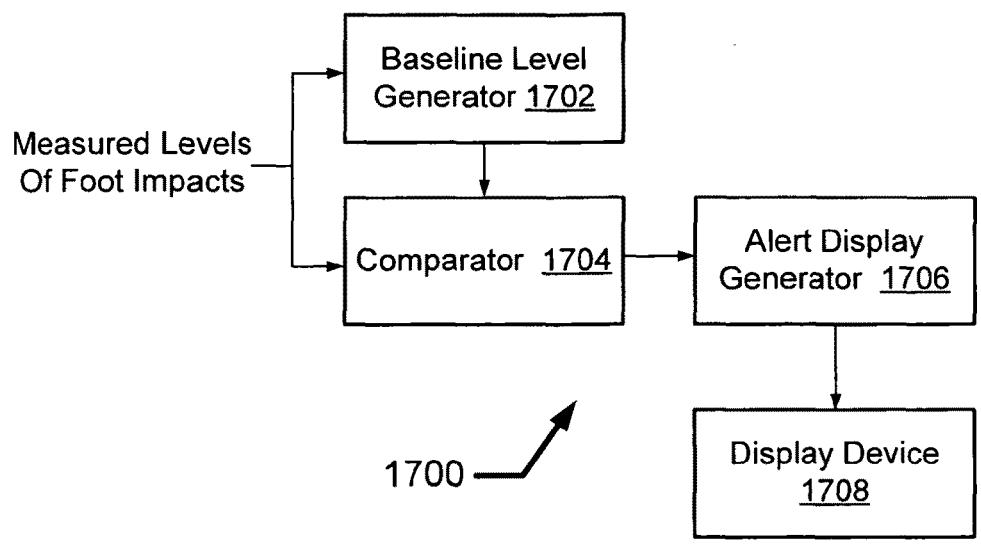
FIG. 17 is a block diagram of a foot impact alert circuit that generates visual indicia that notify a runner/walker of measured foot impact levels while running/walking according to some embodiments of the present invention.

FIG. 17 is a block diagram of a foot impact alert circuit 1700 that generates visual indicia that notify a runner/walker of measured foot impact levels while running/walking according to some embodiments of the present invention. The alert circuit 1700 can include a baseline level generator 1702, comparator 1704, an alert display generator 1706. The baseline level generator 1702 is configured to generate a baseline threshold level in response to an average of measurements of the levels of impact, which are received from a foot impact measurement circuit. The baseline level generator 1702 may respond to a calibration signal from a person (e.g., by a person entering a command to calibrate the system for a new or different pair of shoes) by generating a baseline threshold level in response to an average of measurements of the levels of impact. Alternatively or additionally, the baseline level generator 1702 may generate the baseline threshold level as a running average over a defined interval. The comparator 1704 may compare measured levels of foot impact to the baseline threshold level and cause the alert display generator 1706 to generate an foot impact warning indicia on the display device 1708 that informs the person whether they are experiencing a higher or lower foot impact than the baseline threshold level (e.g., when the measured levels of impact exceed the baseline threshold level).

Accordingly, using the foot impact alert circuit 1700 of FIG. 17, the person can be visually warned when the person's feet are impacting the surface at levels that exceed a baseline threshold level. The person may cause calibration of the baseline threshold level while the person is running with a pair of shoes having a desired level of cushioning and/or while the person is running with a level of foot impact that the person finds to be in a acceptable level and/or an upper range of an acceptable level, above which the person wants the circuit 1700 to display an visible warning so that the person can take action to reduce the impact levels.

Figure 18:
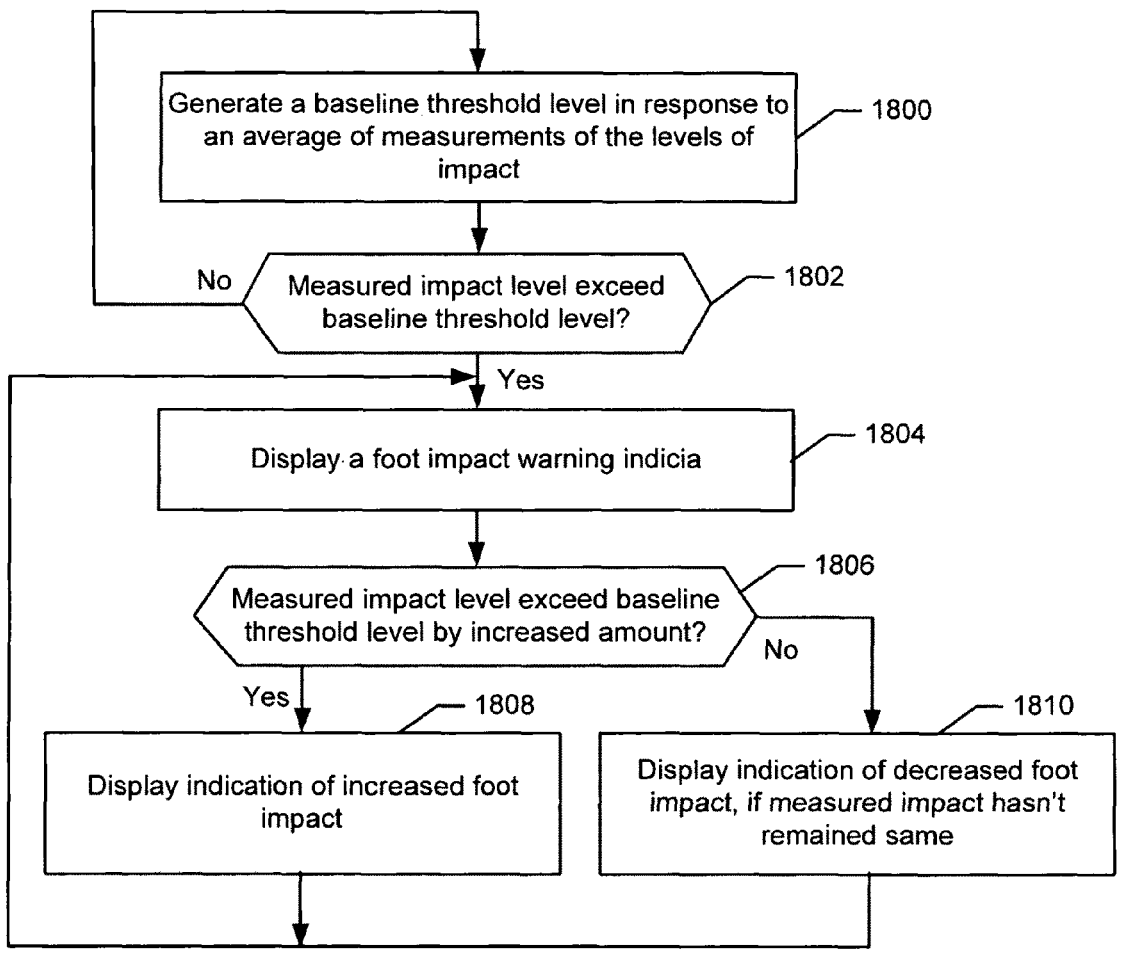
FIG. 18 is a flowchart of operations and methods that generate visual indicia that notify a runner/walker of measured foot impact levels while running/walking according to some embodiments of the present invention.

FIG. 18 is a flowchart of operations and methods for displaying a foot impact warning indicia (e.g., textual warning/symbol/etc.) to a person and regulates what is displayed responsive to measured levels of foot impact while walking/running. Referring to FIG. 18, a foot impact alert circuit (e.g., alert circuit 1700) generates (block 1800) a baseline threshold level in response to an average of measurements of the levels of impact. A decision (block 1802) is made as to whether the measured impact level exceeds the baseline threshold level and, if so, a foot impact warning indicia is displayed (block 1804) to the person. The operations may include a further decision (block 1806) is made as to whether the measured impact level exceeds the baseline threshold level by an increasing or decreasing amount.

When the measured level of the impact exceeds the baseline threshold level by an increased amount, the impact alert circuit 1700 responds (block 1808) by displaying an indication that the level of impact from the foot striking the surface has increased. In contrast, when the measured level of the impact exceeds the baseline threshold level by a decreased amount, the impact alert circuit 1700 responds (block 1810) by displaying an indication that the level of impact from the foot striking the surface has decreased. When the measure level of the impact has not changed relative to the baseline threshold level, the displayed indication may be maintained that same as the indication from the previous iteration.

In some embodiments, the impact alert circuit 1700 may generate one or more of the foot impact information display(s) 20 of FIG. 1 or another display that operates to visually inform a person whether their feet are impacting a surface harder or softer.

In some embodiments, the impact alert circuit is further configured to inform the person of a rate of change of a peak pulse of the measured impact (e.g., the peak pulse shown in the example graph 700 of FIG. 7). The impact alert circuit may generate a baseline threshold level in response to an average of rate of change of the peak pulse of the measured impact, and may respond to a presently measured rate of change of the peak pulse of the measured impact exceeding the baseline threshold level by generating an audible warning through a sound generation device and/or a visual warning through a display device. Generating the warnings in response to the rate of change of the peak pulse may be advantageous because the rate of change of acceleration (e.g., jerk) can indicate the magnitude of shocks that are being transmitted through the person's muscular, tendon, and skeletal structure of the feet, legs, and body, and may be a more accurate predictor of the likelihood of that a running/walking related injury will result if remedial actions are not taken by the person. Accordingly, one, some, or all of the embodiments of the invention disclosed herein can be configured to operate responsive to the rate of change of the peak pulse of the measured impact.

In some further embodiments, the circuits and operations of FIGS. 11-18 may be configured to alternatively or additionally sense whether and how much the person is running/walking with a foot overpronation or supination, and to notify the person using audio and/or visual indications as described in one or more of FIGS. 11-18. Accordingly, the circuits and operations may notify the person of the existence or amount of overpronation/supination by controlling the level of a notification sound that is combined with a music/audio component (e.g., FIGS. 14-16), by controlling the relative loudness of the notification sound, and/or by controlling an alert display (e.g., FIGS. 17 and 18) responsive to the measured overpronation/supination of the foot striking the surface.

In the above-description of various embodiments of the present invention, it is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present invention.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

Exemplary embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks.

A tangible, non-transitory computer-readable medium may include an electronic, magnetic, optical, electromagnetic, or semiconductor data storage system, apparatus, or device. More specific examples of the computer-readable medium would include the following: a portable computer diskette, a random access memory (RAM) circuit, a read-only memory (ROM) circuit, an erasable programmable read-only memory (EPROM or Flash memory) circuit, a portable compact disc read-only memory (CD-ROM), and a portable digital video disc read-only memory (DVD/BlueRay).

The computer program instructions may also be loaded onto a computer and/or other programmable data processing apparatus to cause a series of operational steps to be performed on the computer and/or other programmable apparatus to produce a computer-implemented process such that the instructions which execute on the computer or other programmable apparatus provide steps for implementing the functions/acts specified in the block diagrams and/or flowchart block or blocks.

Accordingly, embodiments of the present invention may be embodied in hardware and/or in software (including firmware, resident software, micro-code, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated. Moreover, although some of the diagrams include arrows on communication paths to show a primary direction of communication, it is to be understood that communication may occur in the opposite direction to the depicted arrows.

Many different embodiments have been disclosed herein, in connection with the above description and the drawings. It will be understood that it would be unduly repetitious and obfuscating to literally describe and illustrate every combination and subcombination of these embodiments. Accordingly, the present specification, including the drawings, shall be construed to constitute a complete written description of various exemplary combinations and subcombinations of embodiments and of the manner and process of making and using them, and shall support claims to any such combination or subcombination.

Many variations and modifications can be made to the embodiments without substantially departing from the principles of the present invention. All such variations and modifications are intended to be included herein within the scope of the present invention.

What is claimed:

1. A foot impact monitoring system comprising:
an impact measurement circuit configured to measure impact from a foot repetitively striking a surface while a person is walking/running; and
an impact alert circuit that is configured to regulate a background sound component in response to measured impacts, and to combine the background sound component with a music component generated by a music player to generate a combined signal that is played to the person to audibly indicate to the person how much impact occurred from the foot striking the surface.

2. The foot impact monitoring system of claim 1, wherein:
the impact measurement circuit comprises an accelerometer configured to measure acceleration and/or rate of change of acceleration as the measured impact from the foot striking the surface while the person is walking/running.

3. The foot impact monitoring system of claim 1, wherein:
the impact measurement circuit comprises a force transducer configured to measure force as the measured impact from the foot striking the surface while the person is walking/running.

4. The foot impact monitoring system of claim 1, wherein:
the impact alert circuit is configured to regulate the background sound component to generate an indication for the person of a peak magnitude of the measured impact.

5. The foot impact monitoring system of claim 1, wherein:
the impact alert circuit is further configured to generate a baseline threshold level in response to measured impacts, and to respond to a presently measured impact exceeding the baseline threshold level by causing the background sound component signal to be audible within the combined signal played through the music player to the person to provide an audible warning to the person when the measured impact from the foot striking the surface has become excessive.

6. The foot impact monitoring system of claim 1, wherein:
the impact alert circuit is further configured to:
generate at least one baseline threshold level in response to measured impacts;
increase loudness of the background sound component relative to the music component of the combined signal being played to the person in response to a presently measured impact exceeding one of the at least one baseline threshold level by an increased amount to audibly indicate to the person when the presently measured impact from the foot striking the surface has increased; and decrease loudness of the background sound component relative the music component of the combined signal being played to the person in response to a presently measured impact exceeding one of the at least one baseline threshold level by a decreased amount to audibly indicate to the person when the presently measured impact from the foot striking the surface has decreased.

7. A foot impact monitoring system comprising:
an impact measurement circuit configured to measure impact from a foot repetitively striking a surface while a person is walking/running;
a sound generation device that is configured to generate sound to the person,
an impact alert circuit that is configured to:
   generate at least one baseline threshold level in response to measured impacts;
   respond to a presently measured impact exceeding one of the at least one baseline threshold level by causing the sound generation device to generate a foot impact warning sound to the person;
   increase loudness and/or modify a defined tone characteristic of the foot impact warning sound generated by the sound generation device in response to a presently measured impact exceeding one of the at least one baseline threshold level by an increased amount to audibly indicate to the person when the presently measured impact from the foot striking the surface has increased; and
   decrease loudness and/or oppositely modify the defined tone characteristic of the foot impact warning sound generated by the sound generation device in response to a presently measured impact exceeding one of the at least one baseline threshold level by a decreased amount to audibly indicate to the person when the presently measured impact from the foot striking the surface has decreased.

8. The foot impact monitoring system of claim 1, further comprising:
a display device configured to display indicia to the person, wherein the impact alert circuit is further configured to:
   generate a baseline threshold level in response to a numeric combination of measured impacts; and
   respond to a presently measured impact exceeding the baseline threshold level by causing the display device to display a foot impact warning indicia to the person.

9. A foot impact monitoring system comprising:
an impact measurement circuit configured to measure impact from a foot repetitively striking a surface while a person is walking/running;
a display device configured to display indicia to the person; and
an impact alert circuit that is configured to:
   generate at least one baseline threshold level in response to measured impacts;
   respond to a presently measured impact exceeding one of the at least one baseline threshold level by causing the display device to display a foot impact warning indicia to the person; and
   cause the display device to modify the foot impact warning indicia to indicate when a presently measured impact is exceeding one of the at least one baseline threshold level by a greater amount, and to indicate when a presently measured impact is exceeding one of the at least one baseline threshold level by a lesser amount to provide visual guidance to the person of the measured impact from the foot striking the surface.

10. The foot impact monitoring system of claim 1, further comprising:
a display device configured to display indicia to the person, wherein the impact alert circuit is further configured to:
   generate a record of the measured impacts; and
   communicate the record of the measured impacts for operation by the display device to graph the measured impacts from the record relative to an elapsed time of the activity, a speed at which the person was walking/running, a stride step distance, and/or a distance that the person walked/ran.

11. The foot impact monitoring system of claim 1, wherein:
the impact alert circuit is configured to regulate the background sound component to inform the person of a rate of change of measurements of an impact.

12. A foot impact monitoring system comprising:
an impact measurement circuit configured to measure impact from a foot repetitively striking a surface while a person is walking/running; and
an impact alert circuit that is configured to:
   generate a baseline threshold level in response to rate of change of measurements of an impact; and
   respond to a present rate of change of measurements of an impact exceeding the baseline threshold level by generating an audible warning through a sound generation device and/or a visual warning through a display device.

13. The foot impact monitoring system of claim 1, wherein the impact alert circuit is further configured to:
   generate an accumulated impact metric in response to the measured impacts; and
   communicate the accumulated impact metric to a display device for display to the person.

14. The foot impact monitoring system of claim 1, wherein the impact alert circuit is further configured to:
   monitor the measured impacts while the person is walking/running over the life of at least one of the person's shoes; and
   generate an indication of when the shoe has become worn-out in response to how much the monitored measured impacts change over the life of the shoe.

15. The foot impact monitoring system of claim 14, wherein the impact alert circuit is further configured to:
   respond to a calibration signal by generating a baseline threshold level in response to measured impacts; and
   generate an indication of when the shoe has become worn-out in response to how much the monitored measured impacts change relative to the baseline threshold level.

16. The foot impact monitoring system of claim 15, wherein the impact alert circuit is further configured to:
   generate the baseline threshold level in response to a numeric combination of measured impacts over more than one minute; and
   generate an indication of when the shoe has become worn-out in response to how much a present numeric combination of measured impacts over another at least one minute changed relative to the baseline threshold level.

17. A foot impact monitoring system comprising:
an impact measurement circuit configured to measure impact from a foot repetitively striking a surface while a person is walking/running; and an impact alert circuit that is configured to:
  monitor the measured impacts while the person is walking/running over the life of at least one of the person's shoes;
  respond to a calibration signal from a person by generating a baseline threshold level in response to rate of change of measurements of impacts; and
  generate an indication of when the shoe has become worn-out in response to a comparison of rate of change of measurements of at least one impact to the baseline threshold level.

18. The foot impact monitoring system of claim 1, wherein:
the impact measurement circuit is configured to be mounted on the person's shoe to increase sensitivity of the impact measurement from the foot striking the surface while the person is walking/running, and
the impact alert circuit comprises a wrist watch.

19. A foot impact monitoring system comprising:
an impact measurement circuit configured to measure impact from a foot repetitively striking a surface while a person is walking/running; and
an impact alert circuit that is configured to:
  determine from characteristics of the measured impact when the person is placing the foot improperly forward when striking the surface and resulting in excessive undesirable slowing forces exerted on the foot and retarding forward movement of the person; and
  generate an audible/visual warning to the person that a first improper foot placement condition exists responsive to the determination that the person is placing the foot improperly forward when striking the surface.

20. The foot impact monitoring system of claim 19, wherein:
the impact alert circuit is further configured to determine that the person is placing the foot improperly forward when striking the surface in response to determining from the measured impact when acceleration greater than a defined threshold occurs in a direction opposite to a forward direction of movement of the person.

21. The foot impact monitoring system of claim 19, wherein the impact alert circuit is further configured to:
determine from characteristics of the measured impact when the person is placing the foot with overpronation or supination when striking the surface and resulting in undesirable rotational forces exerted on the foot; and
generate another audible/visual warning to the person that a second improper foot placement condition exists responsive to the determination that the person is placing the foot with overpronation or underpronation when striking the surface.

22. The foot impact monitoring system of claim 1, wherein:
the impact alert circuit is configured to regulate loudness and/or pitch of white noise as the background sound component.

23. The foot impact monitoring system of claim 1, wherein:
the impact alert circuit is configured to regulate loudness and/or pitch of a repeating tone as the background sound component.

24. The foot impact monitoring system of claim 1, wherein:
the impact alert circuit is configured to regulate loudness of the background sound component relative to the music component of the combined signal being played to the person in response to comparison of measured impacts to at least one baseline threshold level.

25. The foot impact monitoring system of claim 24, wherein:
the impact alert circuit is configured to generate the at least one baseline threshold level in response to measured impacts.

26. The foot impact monitoring system of claim 25, wherein the impact alert circuit is further configured to generate the baseline threshold level in response to a numeric combination of measured impacts.

27. The foot impact monitoring system of claim 25, wherein:
the impact alert circuit is configured to initiate generation of the at least one baseline threshold level in response to a calibration signal.

28. The foot impact monitoring system of claim 7, wherein:
the impact alert circuit is configured to regulate loudness of the foot impact warning sound generated by the sound generation device in response to comparison of measured impacts to one of the at least one baseline threshold level.

29. The foot impact monitoring system of claim 28, wherein:
the impact alert circuit is configured to regulate loudness of white noise generated by the sound generation device in response to comparison of measured impacts to one of the at least one baseline threshold level.

30. The foot impact monitoring system of claim 28, wherein:
the impact alert circuit is configured to regulate loudness of a repeating tone generated by the sound generation device in response to comparison of measured impacts to one of the at least one baseline threshold level.

31. The foot impact monitoring system of claim 7, wherein:
the impact alert circuit is configured to regulate a defined tone characteristic of the foot impact warning sound generated by the sound generation device in response to comparison of measured impacts to one of the at least one baseline threshold level.

32. The foot impact monitoring system of claim 7, wherein:
the impact alert circuit is configured to generate one of the at least one baseline threshold level in response to a numeric combination of measured impacts.

33. The foot impact monitoring system of claim 7, wherein:
the impact alert circuit is configured to generate one of the at least one baseline threshold level in response a calibration process.

34. The foot impact monitoring system of claim 7, further comprising:
a display device configured to display indicia to the person, wherein the impact alert circuit is configured to respond to a presently measured impact exceeding one of the at least one baseline threshold level by causing the display device to display a foot impact warning indicia to the person.

35. The foot impact monitoring system of claim 7, wherein:
the impact measurement circuit is configured to be mounted on a shoe to increase sensitivity of the impact measurement from the foot striking the surface while the person is walking/running, and
the impact alert circuit comprises a wrist watch.

36. The foot impact monitoring system of claim 9, wherein:
the impact alert circuit is configured to display the foot impact warning indicia to indicate a result of comparison of measured impacts to one of the at least one baseline threshold level.

37. The foot impact monitoring system of claim 9, wherein:
the impact alert circuit is configured to generate one of the baseline threshold level in response to a numeric combination of measured impacts.

38. The foot impact monitoring system of claim 9, wherein:
the impact alert circuit is configured to generate one of the at least one baseline threshold level in response a calibration process.

39. The foot impact monitoring system of claim 9, wherein:
the impact alert circuit is configured to graph on the display device the measured impacts relative an elapsed time of the activity, a speed at which the person was walking/running, a stride step distance, and/or a distance that the person walked/ran.

40. The foot impact monitoring system of claim 39, wherein:
the impact alert circuit is configured to graph the measured impacts relative to at least one of the at least one baseline threshold level.

41. The foot impact monitoring system of claim 9, wherein:
the impact alert circuit is configured to modify the foot impact warning indicia by changing distance between a first object displayed on the display device and a second object displayed on the display device responsive to comparison of at least one measured impact and one of the at least one baseline threshold level.

42. The foot impact monitoring system of claim 9, wherein:
the impact alert circuit is configured to modify the foot impact warning indicia by changing shading of at least one object displayed on the display device.

43. The foot impact monitoring system of claim 42, wherein:
the impact alert circuit is configured to modify the foot impact warning indicia by changing shading of a plurality of overlapping objects displayed on the display device.

44. The foot impact monitoring system of claim 43, wherein:
the impact alert circuit is configured to modify the foot impact warning indicia by changing shading of a plurality of concentric circles displayed on the display device.

45. The foot impact monitoring system of claim 9,
wherein the impact alert circuit is configured to:
generate a record of the measured impacts; and
communicate the record of the measured impacts for operation by the display device and/or another display device to graph the measured impacts from the record relative to an elapsed time of the activity, a stride step distance, a speed at which the person was walking/running, and/or a distance that the person walked/ran.

46. The foot impact monitoring system of claim 9, wherein the impact alert circuit is configured to:
monitor the measured impacts while the person is walking/running over the life of at least one of the person's shoes; and
generate a shoe life indication of how much shoe cushioning life remains in response to how much the monitored measured impacts change over the life of the shoe.

47. The foot impact monitoring system of claim 46, wherein:
the impact alert circuit is configured to display the shoe life indication on the display device to indicate how much shoe cushioning life remains and/or when the shoe has become worn out.

48. The foot impact monitoring system of claim 46, wherein:
the impact alert circuit is configured to generate another audible warning through a sound generation device as the indication of when the shoe has become worn-out.

49. The foot impact monitoring system of claim 46, wherein:
the impact alert circuit is configured to generate the indication of how much shoe cushioning life remains in response to how much the monitored measured impacts change relative to one of the at least one baseline threshold level.

50. The foot impact monitoring system of claim 9, wherein:
the impact measurement circuit is configured to be mounted on a shoe to increase sensitivity of the impact measurement from the foot striking the surface while the person is walking/running, and
the impact alert circuit comprises a wrist watch.

51. The foot impact monitoring system of claim 12, wherein:
the impact alert circuit is configured to generate the baseline threshold level in response to a numeric combination of rate of change of measurements of impacts.

52. The foot impact monitoring system of claim 12, wherein:
the impact alert circuit is configured to generate the baseline threshold level in response a calibration process.

53. The foot impact monitoring system of claim 12, wherein:
the impact alert circuit is configured to generate the baseline threshold level in response to rate of change of a pulse segment of measurements of an impact.

54. The foot impact monitoring system of claim 12, wherein:
the impact alert circuit is configured to respond to the present rate of change of measurements of at least one impact exceeding the baseline threshold level by generating an audible warning through the sound generation device.

55. The foot impact monitoring system of claim 12, wherein:
the impact alert circuit is configured to respond to the present rate of change of measurements of at least one impact exceeding the baseline threshold level by generating a visual warning through the display device.

56. The foot impact monitoring system of claim 12, wherein:
the impact alert circuit is configured to regulate loudness of the audible warning through the sound generation device in response to comparison of rate of change of measurements of at least one impact to the baseline threshold level.

57. The foot impact monitoring system of claim 12, wherein:
the impact alert circuit is configured to regulate a defined tone characteristic of the audible warning through the sound generation device in response to comparison of rate of change of the measurements of at least one impact to the baseline threshold level.

58. The foot impact monitoring system of claim 12, wherein:
the impact alert circuit is configured to display the visual warning through the display device to indicate a result of comparison of rate of change of the measurements of at least one impact to the baseline threshold level.

59. The foot impact monitoring system of claim 12, wherein:
the impact alert circuit is configured to graph on the display device an indication of rate of change of measurements of impacts relative an elapsed time of the activity, a stride step distance, a speed at which the person was walking/running, and/or a distance that the person walked/ran.

60. The foot impact monitoring system of claim 12, wherein the impact alert circuit is configured to:
generate a record of the measured impacts; and
communicate the record of the measured impacts for operation by the display device and/or another display device to graph the measured impacts from the record relative to an elapsed time of the activity, a stride step distance, a speed at which the person was walking/running, and/or a distance that the person walked/ran.

61. The foot impact monitoring system of claim 12, wherein the impact alert circuit is configured to:
monitor rate of change of the measurements of impacts while the person is walking/running over the life of at least one of the person's shoes; and
generate an indication of how much shoe cushioning life remains in response to how much the monitored rate of change of the measurements of impacts changes over the life of the shoe.

62. The foot impact monitoring system of claim 61, wherein:
the impact alert circuit is configured to display the indication on the display device to indicate how much shoe cushioning life remains.

63. The foot impact monitoring system of claim 61, wherein:
the impact alert circuit is configured to generate another audible warning through the sound generation device as the indication of how much shoe cushioning life remains and/or when the shoe has become worn out.

64. The foot impact monitoring system of claim 61, wherein:
the impact alert circuit is configured to generate the indication of how much shoe cushioning life remains and/or when the shoe has become worn-out in response to how much the monitored rate of change of the measurements of impacts changes relative to the baseline threshold level.

65. The foot impact monitoring system of claim 12, wherein:
the impact measurement circuit is configured to be mounted on a shoe to increase sensitivity of the impact measurement from the foot striking the surface while the person is walking/running, and
the impact alert circuit comprises a wrist watch.

66. The foot impact monitoring system of claim 17, wherein:
the impact alert circuit is configured to generate the indication of when the shoe has become worn-out by displaying on a display device an indication of how much shoe cushioning life remains in response to change of a pulse segment of measurements of at least one impact.

67. The foot impact monitoring system of claim 66, wherein:
the impact alert circuit is configured to control an amount that an object displayed on a display device is filled-in or emptied to graphically indicate how much cushioning life remains in the shoe.

68. The foot impact monitoring system of claim 66, wherein:
the impact alert circuit is configured to generate the indication of how much shoe cushioning life remains in response to change of a rate of change of a peak pulse segment of measurements of impacts.

69. The foot impact monitoring system of claim 17, wherein:
the impact alert circuit is configured to generate an indication of how much shoe cushioning life remains in response to comparison of a peak pulse segment to another segment outside the peak pulse segment of measurements of at least one impact.

70. The foot impact monitoring system of claim 17, wherein:
the impact alert circuit is configured to generate an indication of how much shoe cushioning life remains in response to comparison of a peak pulse segment of measurements of an impact to a segment of the measurements of the impact which includes the peak pulse segment.

71. The foot impact monitoring system of claim 17, wherein:
the impact alert circuit is configured to generate an indication of how much shoe cushioning life remains in response to a comparison of rate of change of measurements of impacts to the baseline threshold level.

72. The foot impact monitoring system of claim 17, wherein:
the impact alert circuit is configured to generate the baseline threshold level in response to a numeric combination of rate of change of measurements of impacts.

73. The foot impact monitoring system of claim 17, wherein:
the impact alert circuit is configured to generate the baseline threshold level in response to rate of change of a pulse segment of measurements of impacts.

74. The foot impact monitoring system of claim 17, wherein:
the impact alert circuit is configured to respond to a rate of change of measurements of at least one impact exceeding a threshold level by generating an audible warning through a sound generation device.

75. The foot impact monitoring system of claim 17, wherein:
the impact alert circuit is further configured to regulate loudness of an audible warning generated through a sound generation device in response to comparison of rate of change of measurements of impacts to a threshold level.

76. The foot impact monitoring system of claim 17, wherein:
the impact alert circuit is configured to regulate a defined tone characteristic of an audible warning generated through a sound generation device in response to comparison of rate of change of measurements of impacts to a threshold level.

77. The foot impact monitoring system of claim 17, wherein:
the impact alert circuit is configured to respond to a rate of change of measurements of at least one impact exceeding a threshold level by displaying a visual warning through a display device.

78. The foot impact monitoring system of claim 17, wherein:
the impact alert circuit is configured to graph on a display device an indication of rate of change of measurements of impacts relative an elapsed time of the activity, a stride step distance, a speed at which the person was walking/running, and/or a distance that the person walked/ran.

79. The foot impact monitoring system of claim 17, wherein the impact alert circuit is further configured to generate a record of the measured impacts and to communicate the record of the measured impacts for operation by a display device to graph the measured impacts from the record relative to an elapsed time of the activity, a speed at which the person was walking/running, a stride step distance, and/or a distance that the person walked/ran.

80. The foot impact monitoring system of claim 17, wherein:
the impact measurement circuit is configured to be mounted on the person's shoe to increase sensitivity of the impact measurement from the foot striking the surface while the person is walking/running, and
the impact alert circuit comprises a wrist watch.

81. The foot impact monitoring system of claim 19, wherein the impact alert circuit is further configured to:
generate the audible warning through a sound generation device responsive to the determination that the person is placing the foot improperly forward when striking the surface.

82. The foot impact monitoring system of claim 19, wherein the impact alert circuit is further configured to:
generate the visual warning through a display device responsive to the determination that the person is placing the foot improperly forward when striking the surface.

83. The foot impact monitoring system of claim 19, wherein the impact alert circuit is further configured to:
display the visual warning through a display device in response to comparison of acceleration, in a direction opposite to a forward direction of movement of the person, from the measured impacts to a defined threshold.

84. The foot impact monitoring system of claim 19, wherein:
the impact alert circuit is further configured to graph on a display device an indication of acceleration, along a direction of movement of the person, from the measured impacts relative to an elapsed time of the activity, a speed at which the person was walking/running, a stride step distance, and/or a distance that the person walked/ran.

85. The foot impact monitoring system of claim 19, wherein:
the impact alert circuit is further configured to change distance between a first object displayed on the display device and a second object displayed on the display device responsive to comparison of acceleration, along a direction of movement of the person, indicated by at least one measured impact and a defined threshold.

86. The foot impact monitoring system of claim 19, wherein:
the impact alert circuit is further configured to change distance between a first object displayed on the display device and a second object displayed on the display device responsive to comparison of acceleration, along a direction of movement of the person, indicated by at least one measured impact and a value that represents an ideal impact location of the foot.

87. The foot impact monitoring system of claim 19, wherein the impact alert circuit is further configured to:
generate the visual warning within a foot placement informational display, on a display device, that functions as a foot placement coach while a person is running/walking.

88. The foot impact monitoring system of claim 19, wherein:
the impact alert circuit is configured to generate the visual warning on a display device, the visual warning notifying the person of an extent that the person is placing the foot forward when striking the surface.

89. The foot impact monitoring system of claim 19, wherein:
the impact alert circuit is configured to generate the visual warning on a display device, the visual warning notifying the person of a location along the foot between rear foot and forefoot that is initially striking the surface.

90. The foot impact monitoring system of claim 89, wherein:
the impact measurement circuit measures the back-to-front progression of the impact as the foot impacts the surface and rolls forward; and
the impact alert circuit is configured to generate the visual warning on a display device, the visual warning notifying the person of an extent to which the foot is rolling properly based on the measurements by the impact measurement circuit.

91. The foot impact monitoring system of claim 19, wherein:
the impact alert circuit is configured to generate the visual warning on a display device, the visual warning notifying the person of an extent that the person is placing the foot forward when striking the surface relative to an ideal impact location of the foot forward of the body when striking the surface.

92. The foot impact monitoring system of claim 91, wherein:
the ideal impact location is calibrated based on measured impacts to correspond to a foot strike location that reduces backward impact forces against the foot.

93. The foot impact monitoring system of claim 91, wherein:
the ideal impact location is calibrated based on measured impacts to correspond to a location that provides a desired foot strike location on the foot between rear foot and forefoot.

94. The foot impact monitoring system of claim 19, wherein:
the impact alert circuit is configured to generate the audio warning through a sound generation device, and to regulate loudness of the audio warning in response to comparison of acceleration, along a direction of movement of the person, from the measured impacts to a defined threshold.

95. The foot impact monitoring system of claim 19, wherein:
the impact alert circuit is configured to generate the audio warning through a sound generation device, and to regulate loudness of the audio warning in response to comparison of an extent that the person is placing the foot forward when striking the surface relative to an ideal impact location of the foot.

96. The foot impact monitoring system of claim 95, wherein:
the ideal impact location is calibrated based on measured impacts to correspond to a foot strike location that reduces backward impact forces against the foot and/or to correspond to a location that provides a desired foot strike location on the foot between rear foot and forefoot.

97. The foot impact monitoring system of claim 19, wherein:
the impact alert circuit is configured to generate the audio warning through a sound generation device, and to regulate a defined tone characteristic of the audio warning in response to comparison of acceleration, in a direction opposite to a forward direction of movement of the person, from the measured impacts to a defined threshold.

98. The foot impact monitoring system of claim 19, wherein:
the impact alert circuit is configured to generate the audio warning through a sound generation device, and to regulate a defined tone characteristic of the audio warning in response to comparison of an extent that the person is placing the foot forward when striking the surface relative to an ideal impact location of the foot.

99. The foot impact monitoring system of claim 98, wherein:
the ideal impact location is calibrated based on measured impacts to correspond to a foot strike location that reduces backward impact forces against the foot and/or to correspond to a location that provides a desired foot strike location on the foot between rear foot and forefoot.

100. The foot impact monitoring system of claim 19, wherein the impact alert circuit is further configured to:
generate a record of acceleration, along a direction of movement of the person, from the measured impacts; and
communicate the record for operation by the display device and/or another display device to graph an indication of the acceleration from the record relative to an elapsed time of the activity, a speed at which the person was walking/running, a stride step distance, and/or a distance that the person walked/ran.

101. The foot impact monitoring system of claim 19, wherein:
the impact measurement circuit is configured to be mounted on a shoe to increase sensitivity of the impact measurement from the foot striking the surface while the person is walking/running, and
the impact alert circuit comprises a wrist watch.

102. The foot impact monitoring system of claim 19, further comprising:
a tilt sensor that measures an angle of a shoe relative to the direction of movement when the shoe impacts the surface,
wherein the impact alert circuit generates an audible/visual warning to the person that provides an indication of a strike angle of the shoe based on the measured angle.

103. The foot impact monitoring system of claim 20, wherein:
the impact alert circuit is further configured to generate the defined threshold in response to measurements of impacts in response to a calibration process.

104. The foot impact monitoring system of claim 21, wherein:
the impact alert circuit is configured to generate the another visual warning on a display device, the another visual warning notifying the person of an extent that the person is placing the foot with overpronation or supination when striking the surface.

105. The foot impact monitoring system of claim 21, wherein:
the impact alert circuit is configured to configured to graph on the display device an indication of an extent that the person is placing the foot with overpronation or supination when striking the surface relative an elapsed time of the activity, a speed at which the person was walking/running, a stride step distance, and/or a distance that the person walked/ran.

106. The foot impact monitoring system of claim 21, wherein:
the impact alert circuit is configured to generate the another visual warning to notify the person of an extent that the person is placing the foot with overpronation or supination when striking the surface relative to an ideal foot plant angle.

107. The foot impact monitoring system of claim 21, wherein:
the impact alert circuit is configured to generate the another audible warning through a sound generation device, and to regulate a defined tone characteristic and/or a loudness of the another audible warning to notify the person of an extent that the person is placing the foot with overpronation or supination when striking the surface.

108. The foot impact monitoring system of claim 21, wherein:
the impact measurement circuit is configured to measure sideways rolling movement after the foot strikes the ground; and
the impact alert circuit is configured to generate the another visual warning on a display device to notify the person of an extent of the measured sideways rolling movement.

109. The foot impact monitoring system of claim 108, wherein:
the impact alert circuit is configured to generate the another visual warning on the display device in response to comparison of a peak pulse segment to another segment of measurements of the sideways rolling movement.

110. The foot impact monitoring system of claim 108, wherein:
the impact alert circuit is configured to generate the another visual warning on the display device in response to comparison of the peak pulse segment to the another segment which is outside the peak pulse segment of measurements of the sideways rolling movement.

* * * * *